(12) United States Patent
Burnett

(10) Patent No.: US 8,517,973 B2
(45) Date of Patent: *Aug. 27, 2013

(54) IMPLANTABLE FLUID MANAGEMENT SYSTEM FOR THE REMOVAL OF EXCESS FLUID

(75) Inventor: Daniel R. Burnett, San Francisco, CA (US)

(73) Assignee: Sequana Medical AG, Zug (CH)

(*) Notice: Subject to any disclaimer, the term of this patent is extended or adjusted under 35 U.S.C. 154(b) by 248 days.

This patent is subject to a terminal disclaimer.

(21) Appl. No.: 13/029,069

(22) Filed: Feb. 16, 2011

(65) Prior Publication Data

US 2011/0178455 A1    Jul. 21, 2011

Related U.S. Application Data

(63) Continuation of application No. 10/826,237, filed on Apr. 17, 2004, now Pat. No. 7,909,790, which is a continuation of application No. 10/700,863, filed on Nov. 3, 2003, now Pat. No. 7,311,690, and a continuation-in-part of application No. 10/369,550, filed on Feb. 21, 2003, now Pat. No. 7,335,179.

(60) Provisional application No. 60/496,441, filed on Aug. 21, 2003, provisional application No. 60/389,346, filed on Jun. 18, 2002, provisional application No. 60/359,287, filed on Feb. 25, 2002.

(51) Int. Cl.
*A61M 5/00* (2006.01)

(52) U.S. Cl.
USPC .................................. 604/9; 604/8

(58) Field of Classification Search
USPC .............. 604/7–10, 19, 30, 48, 93.01, 94.01, 604/95.01, 96.01, 104, 245–247, 264, 500–508, 604/514, 517, 540, 544; 623/3.1, 3.26, 3.28, 623/11.11, 23.64, 23.65; 128/898
See application file for complete search history.

(56) References Cited

U.S. PATENT DOCUMENTS

| 3,233,610 A | 2/1966 | Wade |
| 3,516,410 A | 6/1970 | Hakim |

(Continued)

FOREIGN PATENT DOCUMENTS

| GB | 2 350 794 | 12/2000 |
| JP | 52-070786 | 10/1993 |

(Continued)

OTHER PUBLICATIONS

Costanzo et al., "Early Ultrafiltration in Patients with Decompensated Heart Failure and Diuretic Resistance," J. Am. Coll. Cardiol., vol. 46 (11), pp. 2047-2051 (2005).

(Continued)

*Primary Examiner* — Philip R Wiest
(74) *Attorney, Agent, or Firm* — Foley & Lardner LLP; Nicola A. Pisano; Christopher C. Bolten

(57) ABSTRACT

An implantable fluid management device, designed to drain excess fluid from a variety of locations in a living host into a second location within the host, such as the bladder of that host. The device may be used to treat ascites, chronic pericardial effusions, normopressure hydrocephalus, hydrocephalus, pulmonary edema, or any fluid collection within the body of a human, or a non-human mammal.

20 Claims, 19 Drawing Sheets

(56) References Cited

U.S. PATENT DOCUMENTS

| | | | |
|---|---|---|---|
| 3,575,158 A | 4/1971 | Summers |
| 3,608,088 A | 9/1971 | Dorman et al. |
| 3,626,950 A | 12/1971 | Schulte |
| 3,654,932 A | 4/1972 | Newkirk et al. |
| 3,669,116 A | 6/1972 | Heyer |
| 3,810,259 A | 5/1974 | Summers |
| 3,910,283 A | 10/1975 | Leveen |
| 4,083,786 A | 4/1978 | Tsuda et al. |
| 4,240,434 A | 12/1980 | Newkirk |
| 4,261,341 A | 4/1981 | Hakim et al. |
| 4,368,737 A | 1/1983 | Ash |
| 4,416,657 A | 11/1983 | Berglund |
| 4,468,219 A | 8/1984 | George et al. |
| 4,557,724 A | 12/1985 | Gregonis et al. |
| 4,584,994 A | 4/1986 | Bamberger et al. |
| 4,595,390 A | 6/1986 | Hakim et al. |
| 4,610,625 A | 9/1986 | Bunn |
| 4,610,658 A | 9/1986 | Buchwald et al. |
| 4,615,691 A | 10/1986 | Hakim et al. |
| 4,618,343 A | 10/1986 | Polaschegg |
| 4,657,530 A | 4/1987 | Buchwald et al. |
| 4,690,673 A | 9/1987 | Bloomquist |
| 4,725,207 A | 2/1988 | Buchwald et al. |
| 4,779,614 A | 10/1988 | Moise |
| 4,850,955 A | 7/1989 | Newkirk |
| 4,904,236 A | 2/1990 | Redmond et al. |
| 4,950,232 A | 8/1990 | Ruzicka et al. |
| 4,963,129 A | 10/1990 | Rusch |
| 5,021,048 A | 6/1991 | Buckholtz |
| 5,045,057 A | 9/1991 | Van Driessche et al. |
| 5,071,408 A | 12/1991 | Ahmed et al. |
| 5,078,688 A | 1/1992 | Lobodzinski et al. |
| 5,147,281 A | 9/1992 | Thornton et al. |
| 5,167,615 A | 12/1992 | East et al. |
| 5,254,084 A | 10/1993 | Geary |
| 5,356,386 A | 10/1994 | Goldberg et al. |
| 5,360,414 A | 11/1994 | Yarger |
| 5,385,541 A | 1/1995 | Kirsch et al. |
| 5,387,188 A | 2/1995 | Watson et al. |
| 5,395,320 A | 3/1995 | Padda et al. |
| 5,395,350 A | 3/1995 | Summers |
| 5,397,354 A | 3/1995 | Wilk et al. |
| 5,431,637 A | 7/1995 | Okada et al. |
| 5,472,323 A | 12/1995 | Hirabayashi et al. |
| 5,474,683 A | 12/1995 | Bryant et al. |
| 5,489,276 A | 2/1996 | Jamshidi |
| 5,520,632 A | 5/1996 | Leveen et al. |
| 5,575,770 A | 11/1996 | Melsky et al. |
| 5,637,083 A | 6/1997 | Bertrand et al. |
| 5,725,506 A | 3/1998 | Freeman et al. |
| 5,830,172 A | 11/1998 | Leveen et al. |
| 5,902,336 A | 5/1999 | Mishkin |
| 5,947,911 A | 9/1999 | Wong et al. |
| 5,980,478 A | 11/1999 | Gorsuch et al. |
| 5,989,207 A | 11/1999 | Hughes |
| 6,007,511 A | 12/1999 | Prywes |
| 6,017,355 A | 1/2000 | Hessel et al. |
| D420,738 S | 2/2000 | Carter et al. |
| 6,022,333 A | 2/2000 | Kensey |
| 6,132,415 A | 10/2000 | Finch et al. |
| 6,162,238 A | 12/2000 | Kaplan et al. |
| 6,162,487 A | 12/2000 | Darouiche |
| 6,193,684 B1 | 2/2001 | Burbank et al. |
| 6,254,567 B1 | 7/2001 | Treu et al. |
| 6,264,625 B1 | 7/2001 | Rubenstein et al. |
| 6,417,750 B1 | 7/2002 | Sohn |
| 6,436,087 B1 | 8/2002 | Lewis et al. |
| 6,533,733 B1 | 3/2003 | Ericson et al. |
| 6,689,085 B1 | 2/2004 | Rubenstein et al. |
| 6,827,682 B2 | 12/2004 | Bugge et al. |
| 6,846,168 B2 | 1/2005 | Davis |
| 6,875,192 B1 | 4/2005 | Saul et al. |
| 6,887,214 B1 | 5/2005 | Levin et al. |
| 6,894,456 B2 | 5/2005 | Tsukamoto et al. |
| 6,905,474 B2 | 6/2005 | Borgensen |
| 6,926,691 B2 | 8/2005 | Miethke |
| 6,955,655 B2 | 10/2005 | Burbank et al. |
| 7,025,739 B2 | 4/2006 | Saul |
| 7,025,742 B2 | 4/2006 | Rubenstein et al. |
| 7,128,735 B2 | 10/2006 | Weston |
| 7,195,608 B2 | 3/2007 | Burnett |
| 7,311,690 B2 * | 12/2007 | Burnett ............... 604/9 |
| 7,335,179 B2 | 2/2008 | Burnett |
| 7,419,483 B2 | 9/2008 | Shehada |
| 7,909,790 B2 * | 3/2011 | Burnett ............... 604/9 |
| 2001/0025170 A1 | 9/2001 | Paderni |
| 2001/0027289 A1 | 10/2001 | Treu et al. |
| 2002/0013545 A1 | 1/2002 | Soltanpour et al. |
| 2002/0022793 A1 | 2/2002 | Bertrand et al. |
| 2003/0163079 A1 | 8/2003 | Burnett |
| 2004/0049288 A1 | 3/2004 | Levin |
| 2004/0147871 A1 | 7/2004 | Burnett |
| 2005/0096582 A1 | 5/2005 | Burnett |
| 2005/0131340 A1 | 6/2005 | Sorenson et al. |
| 2005/0273034 A1 | 12/2005 | Burnett |
| 2006/0036208 A1 | 2/2006 | Burnett |
| 2006/0058731 A1 | 3/2006 | Burnett et al. |
| 2007/0106205 A1 | 5/2007 | Connell et al. |
| 2008/0108935 A1 | 5/2008 | Nyhart, Jr. |
| 2008/0154173 A1 | 6/2008 | Burnett |
| 2009/0318844 A1 | 12/2009 | Burnett |

FOREIGN PATENT DOCUMENTS

| | | |
|---|---|---|
| JP | 09-056810 | 3/1997 |
| WO | WO 97/41799 | 11/1997 |
| WO | WO 98/16171 | 4/1998 |

OTHER PUBLICATIONS

Houlberg et al., "Terminal Right Heart Failure Due to Complex Congenital Cardiac Disease Successfully Managed by Home Peritoneal Drainage," Cardiol. Young, vol. 13, pp. 568-570 (2003).

Ortiz et al., "Long-Term Automated Peritoneal Dialysis in Patients with Refractory Congestive Heart Failure," Advances in Peritoneal Dialysis, vol. 19, pp. 77-80 (2003).

Rozenblit, "Peritoneal-Urinary Drainage for Treatment of Refractory Ascites: A Pilot Study", NY, Journal of Vascular & Interventional Radiology, 9(6), pp. 998-1005 (Nov./Dec. 1998).

Neragi-Miandoab, "Malignant Pleural Effusion, Current and Evolving Approaches for its Diagnosis and Management", Lung Cancer 54, pp. 1-9 (2006).

Tan et al., "The Evidence on the Effectiveness of Management for Malignant Pleural Effusion: A Systematic Review", European Journal of Cardio-thoracic Surgery 29, pp. 829-838 (2006).

Warren et al., "Management of Malignant Pleural Effusions Using the Pleurx Catheter", Ann. Thrac. Sur. 85, pp. 1049-1055 (2008).

USPTO, Supplemental Notice of Allowability mailed Dec. 19, 2007, U.S. Appl. No. 10/369,550, 2 pages.

USPTO, Notice of Allowance and Fees Due mailed Sep. 24, 2007, U.S. Appl. No. 10/369,550, 3 pages.

USPTO, Final Office Action mailed Dec. 13, 2006, U.S. Appl. No. 10/369,550, 4 pages.

USPTO, Non-Final Office Action mailed Mar. 9, 2006, U.S. Appl. No. 10/369,550, 13 pages.

USPTO, Advisory Action mailed Feb. 25, 2010, U.S. Appl. No. 12/014,696, 3 pages.

USPTO, Final Office Action mailed Jan. 7, 2010, U.S. Appl. No. 12/014,696, 18 pages.

USPTO, Non-final Office Action mailed Apr. 29, 2009, U.S. Appl. No. 12/014,696, 20 pages.

USPTO, Non-Final Office Action mailed Mar. 9, 2006, U.S. Appl. No. 10/922,478.

USPTO, Corrected Notice of Allowance and Fees Due mailed Nov. 8, 2007, U.S. Appl. No. 10/700,863, 2 pages.

USPTO, Notice of Allowance and Fees Due mailed Nov. 2, 2006, U.S. Appl. No. 10/700,863, 3 pages.

USPTO, Non-Final Office Action mailed Feb. 2, 2006, U.S. Appl. No. 10/700,863, 11 pages.

USPTO, Supplemental Notice of Allowability mailed Jan. 9, 2007, U.S. Appl. No. 11/198,079, 2 pages.

USPTO, Notice of Allowance and Fees Due mailed Oct. 5, 2006, U.S. Appl. No. 11/198,079, 3 pages.
USPTO, Non-final Office Action mailed Feb. 2, 2006, U.S. Appl. No. 11/198,079, 7 pages.
USPTO, Notice of Allowance with reasons for allowance mailed Jul. 20, 2009, U.S. Appl. No. 11/181,539, 9 pages.
USPTO, Non-Final Office Action mailed Sep. 16, 2008, U.S. Appl. No. 11/181,539, 10 pages.
USPTO, Advisory Action mailed Jul. 14, 2008, U.S. Appl. No. 11/181,539, 3 pages.
USPTO, Final Office Action mailed Mar. 18, 2008, U.S. Appl. No. 11/181,539, 10 pages.
USPTO, Non-Final Office Action mailed May 22, 2007, U.S. Appl. No. 11/181,539, 8 pages.
USPTO, Final Office Action mailed Oct. 10, 2006, U.S. Appl. No. 11/181,539, 6 pages.
USPTO, Non-Final Office Action mailed Jan. 27, 2006, U.S. Appl. No. 11/181,539, 8 pages.
USPTO, Notice of Allowance mailed Jul. 23, 2010, U.S. Appl. No. 10/826,237, 9 pages.
USPTO, Final Office Action mailed Jan. 5, 2010, U.S. Appl. No. 10/826,237, 13 pages.
USPTO, Non-Final Office Action mailed Apr. 13, 2009, U.S. Appl. No. 10/826,237, 14 pages.
USPTO, Final Office Action mailed Oct. 28, 2008, U.S. Appl. No. 10/826,237, 10 pages.
USPTO, Non-Final Office Action mailed Feb. 22, 2008, U.S. Appl. No. 10/826,237, 10 pages.
USPTO, Advisory Action mailed Nov. 20, 2007, U.S. Appl. No. 10/826,237, 3 pages.
USPTO, Final Office Action mailed Jul. 5, 2007, U.S. Appl. No. 10/826,237, 10 pages.
USPTO, Non-Final Office Action mailed Dec. 19, 2006, U.S. Appl. No. 10/826,237, 8 pages.
USPTO, Non-Final Office Action mailed Apr. 6, 2010, U.S. Appl. No. 11/933,214, 18 pages.
International Search Report mailed Jul. 17, 2003, PCT/US03/05145, 3 pages.
USPTO, Final Office Action mailed Feb. 10, 2011, U.S. Appl. No. 11/933,214, 21 pages.

* cited by examiner

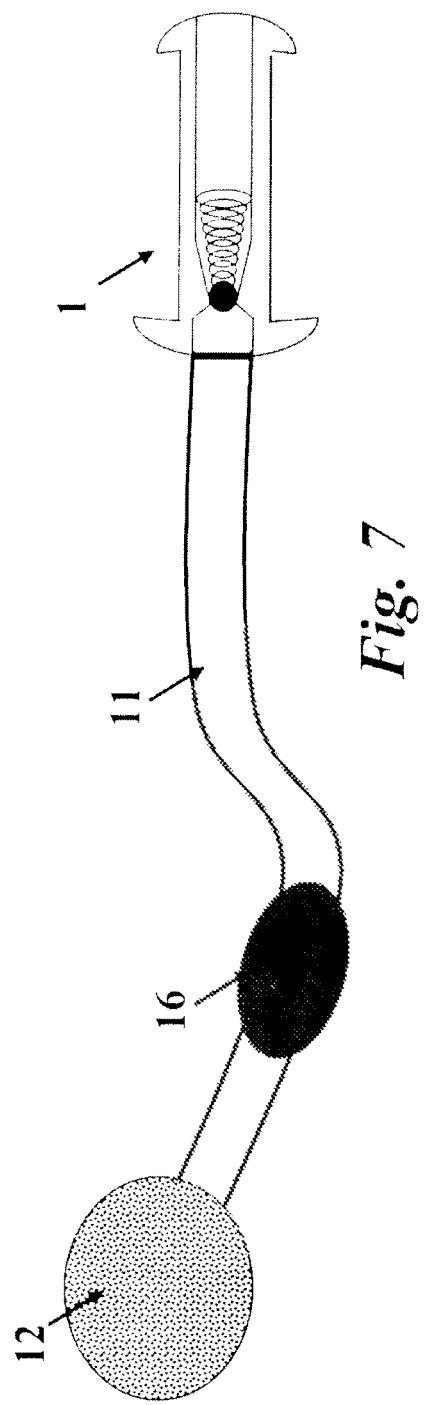

IMPLANTABLE FLUID MANAGEMENT SYSTEM FOR THE REMOVAL OF EXCESS FLUID

CROSS-REFERENCE TO RELATED APPLICATIONS

This application is a continuation of U.S. patent application Ser. No. 10/826,237, filed Apr. 17, 2004, now U.S. Pat. No. 7,909,790, which is a continuation of U.S. patent application Ser. No. 10/700,863, filed Nov. 3, 2003, now U.S. Pat. No. 7,311,690, which claims the benefit of priority to U.S. Provisional Patent Application No. 60/496,441, filed Aug. 21, 2003 and is a continuation-in-part of U.S. patent application Ser. No. 10/369,550, filed Feb. 21, 2003, now U.S. Pat. No. 7,335,179, which claims the benefits of priority to U.S. Provisional Patent Application No. 60/389,346, filed on Jun. 18, 2002, and to U.S. Provisional Patent Application No. 60/359,287, filed on Feb. 25, 2002, the contents of which are incorporated herein by reference in their entirety.

FIELD OF THE INVENTION

The invention is generally in the field of medical devices. More particularly, it relates to implantable pump-assisted drainage devices, e.g., for transvesicluar drainage, capable of draining fluid from a bodily cavity into another bodily cavity, such as a bladder.

BACKGROUND OF THE INVENTION

There are a variety of conditions which result in pathologic chronic collection of bodily fluids within the body of a person. Chronic pericardial effusions, normopressure hydrocephalus, hydrocephalus, chronic pulmonary effusion, pulmonary edema, and ascites are but a few of the conditions in which chronic fluid collections persist and result in increased morbidity and mortality.

These types of conditions currently are treated typically by one of three methods: 1) external drainage with a high-risk of infection and long-term requirement for multiple punctures, 2) drainage to another body cavity, or 3) treatment with various drugs. For pericardial effusions and hydrocephalus of all types, the treatment of choice is typically drainage to another region of the body. For pericardial effusions this entails a pericardial window, a highly invasive procedure in which a large section of the external heart cavity is removed. For hydrocephalus, the treatment typically involves the use of a ventriculo-peritoneal shunt draining the cerebrospinal fluid into the peritoneal cavity. This device frequently becomes clogged due to the proteinaceous environment of the peritoneal cavity and requires removal or revision.

One problem which may arise with the chronic collection of bodily fluids is ascites, which is a highly debilitating complication associated with many medical conditions including liver failure and congestive heart failure. Untreated ascites can result in respiratory compromise, compression of the inferior vena cava (a vital blood vessel) and spontaneous bacterial peritonitis (a life-threatening condition). In order to treat chronic ascites, medicine has turned to both drugs and surgery.

The drugs required to treat ascites are typically long-term and frequently result in complications. The most common pharmaceutical treatment of ascites involves the use of diuretics to remove fluid from the patient's body through their urine. The difficulty with this treatment, though, is that fluid is removed from the entire body, including the circulating volume of blood, and can result in excessive loss of fluid required to perfuse the vital organs of the human body. Thus, even with frequent application, the medicines frequently fail. In such cases, surgical, or invasive; procedures are indicated.

Currently the most common surgical treatment is paracentesis. In paracentesis, the peritoneal fluid is drained through the abdominal wall via the insertion of a needle through the abdominal wall into the peritoneal cavity. This procedure is only a temporary solution as the ascites quickly refills the peritoneal cavity in most chronic conditions. Furthermore, repeated paracenteses places the patient at increased risk for a life-threatening infection of their peritoneal cavity. Other surgical/invasive procedures typically involve treatment of the cause of the ascites (for example, the Transjugular Intrahepatic Portosystemic Shunt) but these measures also frequently result in complications, which are often serious and are thus performed infrequently.

Many of the existing commercially available devices provide little improvement over the intermittent punctures of paracentesis and result in increased rates of infection or other complications if left in place for any length of time. Therefore, there is a need for a device which effectively reduces the need for repeated punctures or abdominal incisions and thereby reduces the risk of serious infection.

SUMMARY OF THE INVENTION

An implantable fluid management system, as described herein, may typically comprise a first tube member having a first end, a second end, and a length which defines a lumen therethrough and having at least one opening at the first end or along the length, a second tube member having a first end, a second end, and a length which defines a lumen therethrough, a pump fluidly coupled to the first tube member and the second tube member for urging fluid through each tube member, and a shunt connected to the second end of the second tube member, wherein the shunt is adapted to anchor the second end of the second tube member to a wall of a hollow body organ in a fluid-tight seal.

This system may avoid difficulties typically associated with the current therapies. For instance, in the treatment of chronic ascites, the devices of the system may allow for the removal of peritoneal fluid without 1) serious complications generally associated with use of pharmaceuticals, 2) inconvenience, for example, the substantial costs and the increased risk of infection associated with frequent paracenteses, or 3) multiple severe complications associated with more invasive and risky surgical operations to treat the cause of ascites. The implantable fluid management system may be utilized for chronic excess fluid drainage from one bodily cavity to a second bodily cavity, e.g., a urinary bladder. An implantable electromechanically powered and/or magnetically coupled vesicular pump may be utilized to permit assisted flow of the excess fluid collections into the bladder. This flow may be directed to be uni-directional through the system.

One particular variation of the system may be used as an ascites drainage device. For instance, the device of the system may be used for peritoneovesicular drainage of the peritoneal fluid from the peritoneal cavity into, e.g., the bladder. The drainage of the fluid may be uni-directional through the system. To urge the fluid through the fluid management system, a pump which is fully implantable may be utilized with the system to transfer excess fluid from a variety of locations in the human body, for instance, the peritoneal cavity, to another region within the body, for instance, the urinary bladder, for the treatment of chronic fluid collections.

The system, including the pump and/or tubular members, may be configured to enable fluid flow in only one direction into, e.g., the bladder, to prevent the reflux of urine or other fluids into the area being drained while still allowing the drainage of the fluid into the bladder. This uni-directional configuration may be achieved through incorporation of a uni-directional valve in the lumen of the tubing or through the use of a uni-directional pump which may also be prevented from being driven in reverse.

The device may include at least two distinct flexible tubular members each defining at least one lumen therethrough. One tubular member may be used for drawing fluid from the region to be drained into or through the pump while the other tube may be used for channeling the fluid from the pump into the hollow body organ such as the bladder. The tube for drawing the excess fluid from the body cavity may contain or define at least one opening, and may preferably define multiple perforations, and/or anti-clogging mechanisms in the region of the fluid intake. This tubular member may also optionally incorporate chemical- or pressure-sensing elements to trigger and/or prevent activation of the pump under specific circumstances. The tubular member carrying the pumped fluid to the bladder may feature an anchoring mechanism such as a shunt mentioned above (e.g., a flange, pigtail coil, etc.) and may optionally be coated with a hydrophilic material to prevent encrustation. The tip of this tubing may also optionally incorporate chemical- or pressure-sensing elements to trigger and/or prevent activation of the pump under specific circumstances ensuring that the pump does not generate excessive bladder pressures. These sensors can be placed anywhere along the length of either tube, including the extremes of a position at the site of pump attachment and a position at the tip of the tubing. Optionally, the two tubes can be integrated together into a single tubular member having two distinct lumens for ease of insertion.

The shunt for anchoring to the bladder wall may, in one variation, comprise a hollow, cylindrical column with flanges at either or both ends to provide secure anchorage in the bladder wall. The shunt may have an integrated mechanism to ensure uni-directional flow of fluid while preventing reflux of urine and other fluids back through the shunt. One variation of the shunt may provide a passive ball-valve mechanism which allows for drainage of fluid into the bladder whenever a certain minimum threshold pressure is achieved at the collection site. Another variation may provide an active valve mechanism which allows for controlled drainage of fluid into the bladder whenever the valve is actuated.

The system can be made available in multiple configurations and designs for varying types and severity of fluid collections. For drainage of excess cerebrospinal fluid, for example, the tubing connecting the pump to the ventricle of the brain may be fabricated to be significantly longer than the tubing for chronic ascites which need only reach an adjacent peritoneal cavity.

The methods of insertion of the fluid management system may be based, in part, on the location of the fluid collection. On the other hand, the tubular member spanning to the bladder wall may be placed, e.g., cystoscopically or transabdominally, using minimally invasive procedures. The pump may be placed subcutaneously using interventional radiology techniques including radiographic imaging such as ultrasound. The inflow tubing connected to the pump, in one variation, may be tunneled subcutaneously to the site of drainage and the outflow tubing can be subcutaneously channeled to the bladder. Alternatively, the pump can be placed in the peritoneal cavity, or other bodily cavity, and activated remotely or set to operate independently based on pressure signals sensed from the fluid. In this variation, the pump may be tethered to an inductive charging coil for recharging or, if a battery with sufficient life is used, may carry its own independent power supply.

The system may also optionally include controls to limit the operation of the pump and provide feedback to ensure that the pump is operating correctly. Thus the total fluid flow can be monitored and tightly controlled.

BRIEF DESCRIPTION OF THE DRAWINGS

FIG. 7 shows a cross-sectional illustration of an alternative variation of the drainage system in which a pump may be included along the length of the tubing.

DETAILED DESCRIPTION OF THE INVENTION

The implantable fluid management system may comprise devices for facilitating the removal of fluid from a body region where drainage is desired. For instance, the devices disclosed herein may be utilized for chronic excess fluid drainage from one bodily cavity to a second bodily cavity, e.g., a urinary bladder. An implantable electromechanically powered and/or magnetically coupled vesicular pump may be utilized to permit assisted flow of the excess fluid collections into the bladder. This flow may be directed to be unidirectional through the system.

Figure 1:
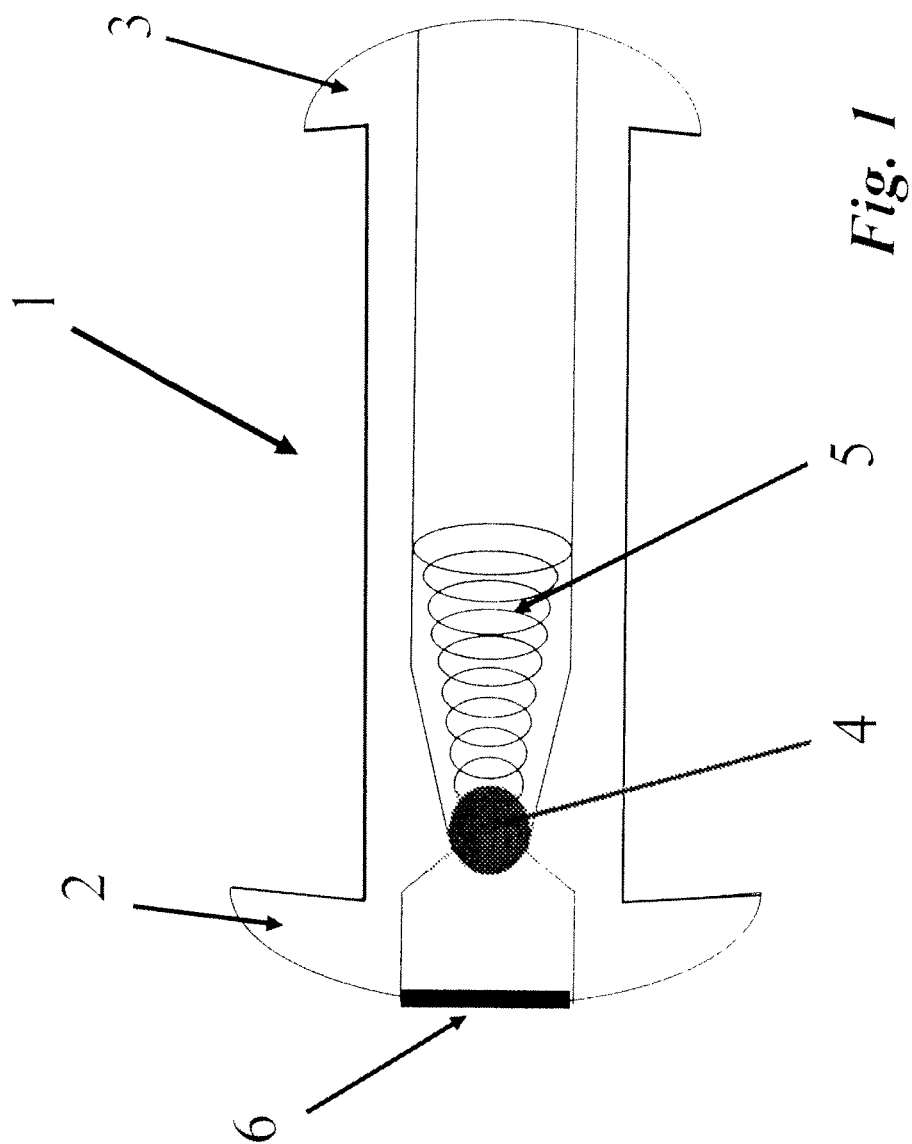
FIG. 1 shows a cross-sectional view of a variation of a shunt device.
Figure 2:
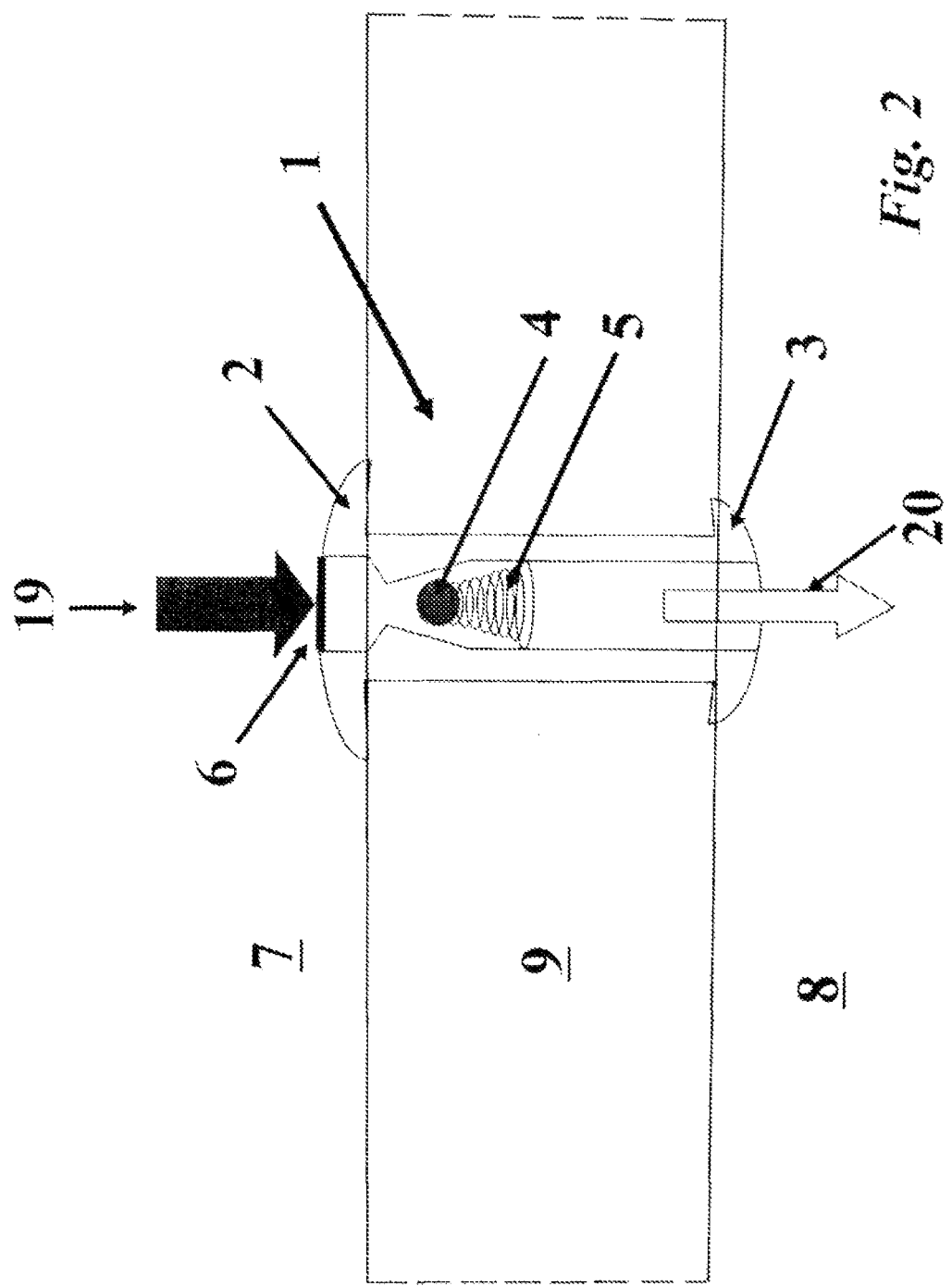
FIG. 2 shows a cross-sectional view of an implanted shunt.

As can be seen in FIG. 1, a vesicular shunt or drain 1 may be utilized with the fluid management system for anchoring a tubing member to the wall of a urinary bladder. A further detailed description of the shunt and its applications may be seen in U.S. application Ser. No. 10/369,550 filed on Feb. 21, 2003, which has been incorporated herein by reference above. Shunt or drain 1 may be implanted in the bladder wall 9, as shown in FIG. 2, and can be configured to provide for unidirectional drainage of fluid into the bladder. In one variation, the shunt or drain 1 may comprise a flange or projection 2, 3 at each end of the shunt 1 to facilitate firmly anchoring the shunt 1 across the bladder wall 9. Alternative variations of the shunt 1 may utilize other anchoring mechanisms, including, but not limited to, screw threading on the outside of shunt 1, staples, sutures, adhesive compounds, one or more barbs, etc., and combinations thereof.

In one variation, the shunt 1 may be configured to define a lumen through the shaft of the device with a valving mechanism positioned within this lumen. For instance, a ball-valve 4 may be positioned to obstruct an inflow opening of the lumen. A biasing element such as a spring 5 may be configured to provide a closing pressure against the ball-valve 4 such that the lumen remains shut until a minimum threshold pressure is developed by the fluid which may force the ball-valve 4 open or until a pump is actuated to open the valve 4. The inflow port of the shunt 1 may optionally include a porous mesh or filter 6 to allow for the free flow of fluid through shunt 1 while preventing the incarceration of tissues at the drainage site. Moreover, the mesh or filter 6 may be configured to filter the fluid through a polymer to sequester components which may be present within the fluid, such as albumin and other proteins, while allowing the flow of fluids and ions across the semi-permeable membrane.

As can be seen in the variation of FIG. 2, once a pressure of the collected peritoneal fluid 19 has built up, in this case within the peritoneal cavity 7, and exceeds the combined threshold force of the spring 5 and a pressure of the fluid-filled bladder cavity 8, the peritoneal fluid 19 may urge the ball-valve 4 open to then allow fluid flow into the bladder 8. Once the peritoneal fluid 19 has entered the bladder, the peritoneal fluid 19 may mix with the urine 20 and any other fluids which may be present. Once a sufficient amount of fluid 19 has passed through shunt 1 and the fluid pressure within the peritoneal cavity 7 falls below the threshold pressure of the spring 5, the ball-valve 4 may be urged shut to prevent further fluid flow through the shunt 1. The spring force exerted by the biasing element to shut the valve 4 within the shunt 1 may be varied depending upon the amount of fluid flow desired.

Figure 3:
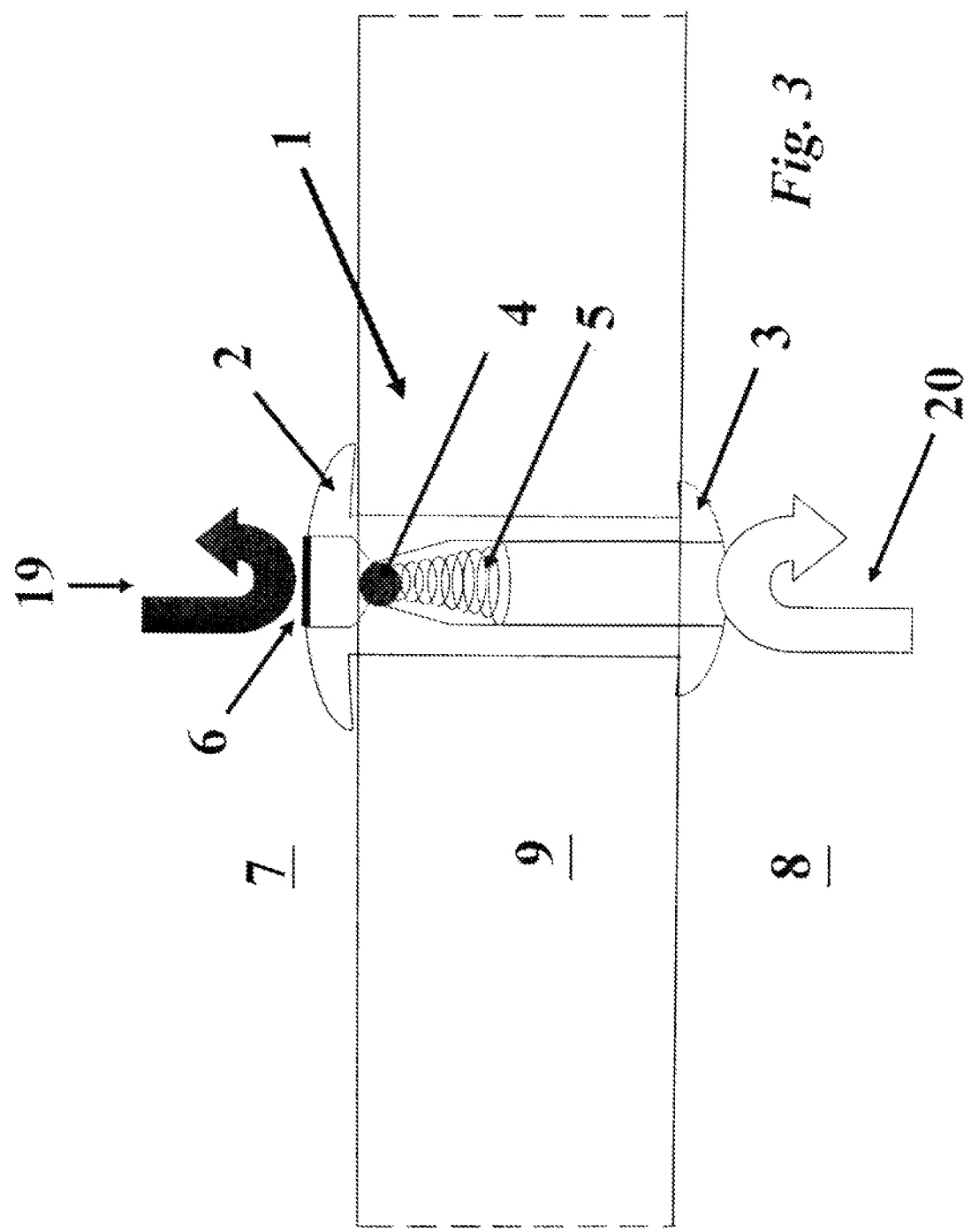
FIG. 3 shows a cross-sectional view of the implanted shunt when the peritoneal fluid pressure is insufficient to open the valve.

If the combined pressure from the fluid pressure within the bladder 8 and the closing force of the spring 5 is greater than the pressure exerted by the collected fluid within the peritoneal cavity 7, then the valve 4 will remain closed preventing reflux of urine and other fluids back into the peritoneal cavity 7, as depicted in FIG. 3.

Figure 4:
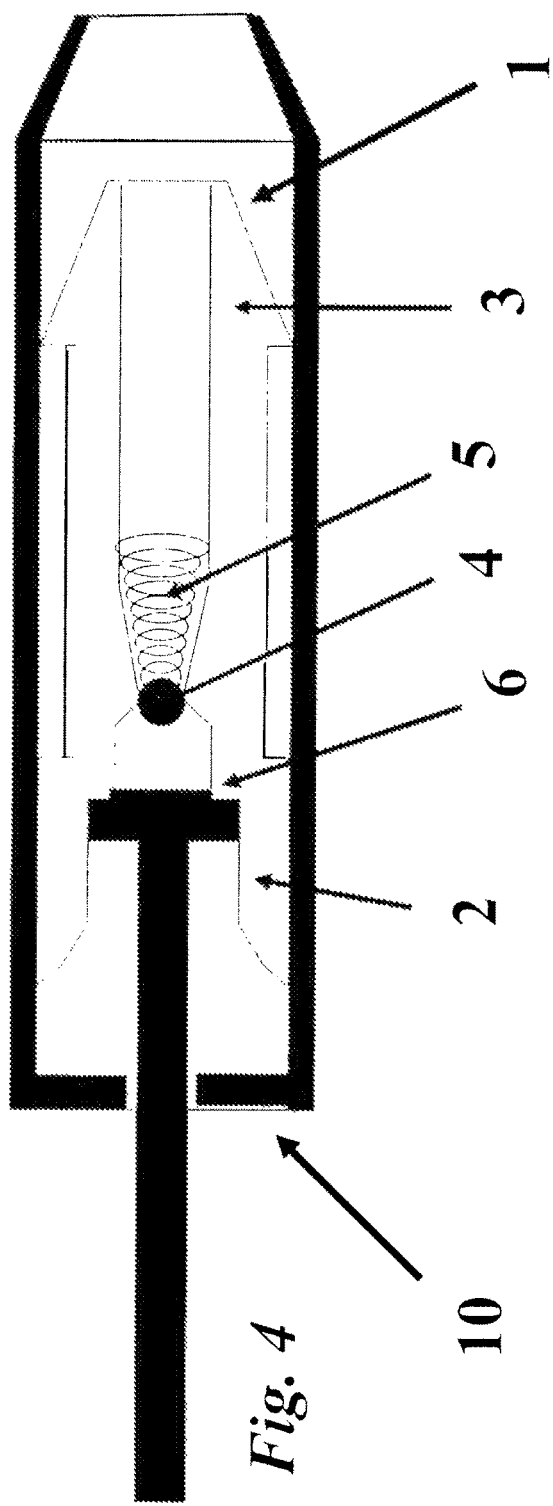
FIG. 4 shows a cross-sectional view in an illustration of an example of an insertion device within which the shunt can be implanted in the bladder wall.

The shunt 1 may be designed to be deployed transurethrally or transabdominally via an insertion device 10, such as that depicted in the variation of FIG. 4. Various devices such as endoscopes, catheters, introducers, etc., may also be utilized as an insertion device 10 depending upon the patient anatomy and the location where the shunt 1 is to be placed. A specially configured insertion device 10 may define a cavity or channel within which the shunt 1 may be positioned for deployment within a patient. The variation shown in the figure may incorporate flexible flanges 2, 3 on one or both ends of the shunt 1. During delivery, one or both flanges 2, 3 may be configured in a low profile configuration and after delivery, one or both flanges 2, 3 may be configured to self-expand or reconfigure into a larger configuration. Accordingly, flanges 2, 3 may optionally be fabricated from spring steels, shape memory alloys and superelastic alloys such as nitinol, etc. Once the distal end of insertion device 10 has been brought into proximity or adjacent to the region of tissue where shunt 1 is to be inserted, the shunt 1 may be urged out of insertion device 10 via a pusher or plunger, as shown in the figure. Alternatively, shunt 1 may be positioned upon the distal end of an insertion device and released into the tissue wall via a release mechanism.

A tubing member 11 may be attached to the inflow port of shunt 1. This tubing member 11 may be made such that it is sufficiently long enough to reach the region within the body where excess fluid collects. As shown in the illustrative drawings in FIGS. 5A to 5C, tubing member 11 may have a perforated receptacle 12, as described in further detail below, through which the collected fluid may drain into the tubing 11. Other methods for fluid transport may include, but are not limited to, conduits, catheters, saphenous arteries or vessels, artificial tubular grafts, etc.

Figures 5A, 5B, 5C:
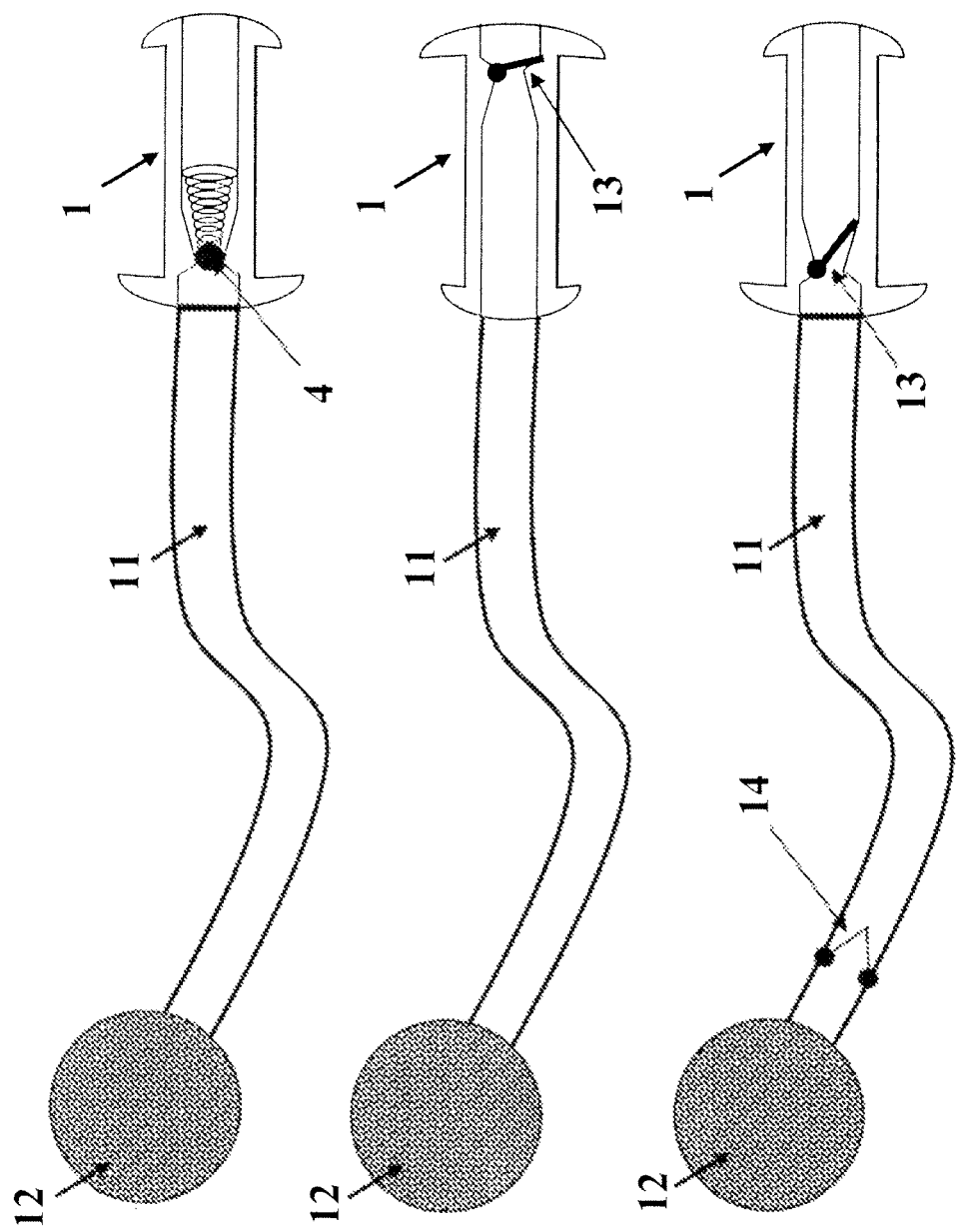
FIGS. 5A to 5C show alternative variations of the fluid management system with differing valve types, differing valve positioning and differing number of valves.

In addition to the shunt 1 having a ball valve 4 in combination with the tubing member 11, other variations may utilize one or more valves of a variety of different types. For instance, passively-actuated valves, i.e., valves which are configured to automatically open and close without being actively actuated, such as the ball-valve 4 shown in FIG. 5A and flapper valve 13 as shown in FIG. 5B. The flapper type valve 13 may be positioned within shunt 1 near the outflow port, as shown in FIG. 5B, or it may also be positioned closer to the inflow port, as shown in FIG. 5C. An additional optional valve 14 may be incorporated into the tubing member 11 anywhere along the length of tubing 11. The types of valves disclosed are intended to be illustrative and is not intended to be limiting. Other variations of the valves are intended to be within the scope of this disclosure.

Figure 6A:
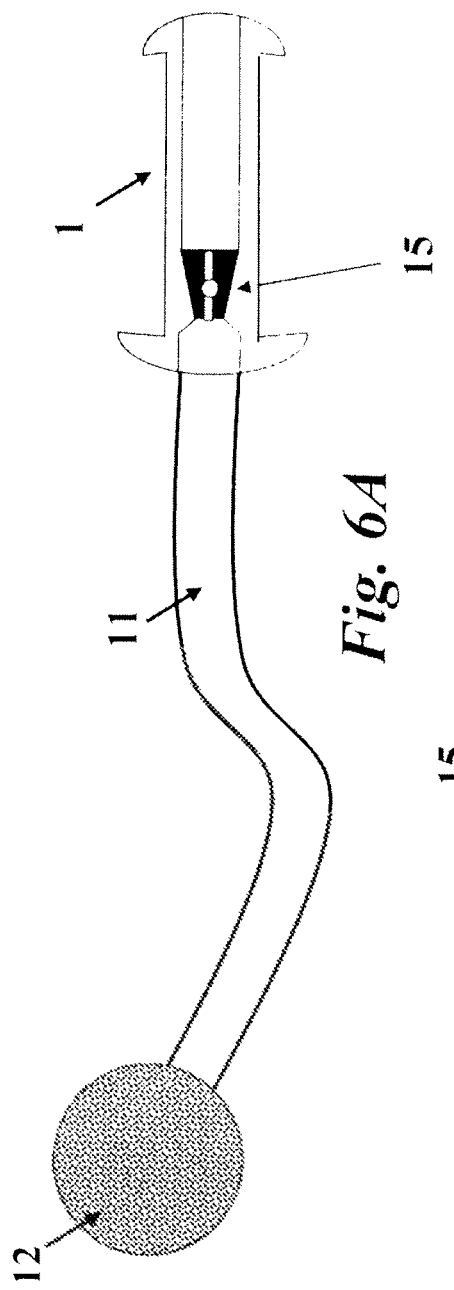
FIGS. 6A and 6B show cross-sectional illustrations of an alternative variation of the system and a detail view of the shunt, respectively, in which an active, externally, or internally controlled valve is utilized.
Figure 6B:
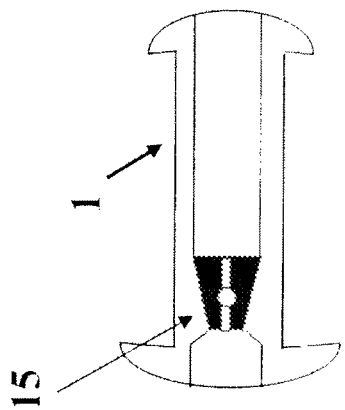

Alternatively, active valves, i.e., valves which may be configured to open and close via an actuation or sensing element, may also be utilized with the fluid management system. The use of active valves may be utilized for maintaining a tighter control of fluid drainage. For instance, FIG. 6A shows one variation of an active valve 15 positioned within the lumen of shunt 1 in combination with the tubular member 11. FIG. 6B shows a cross-sectional side view of the shunt 1 alone having the active valve 15 positioned within. Active valve 15 may be actuatable via a remotely located controller to open and shut upon receiving a signal. Alternatively, sensors positioned within the shunt 1 or within the tubing 11 may provide a signal to the active valve 15 to open or shut according to the signal.

In another variation, an electronic valve may be configured to become triggered via communication across the tissues of the human body through electromagnetic signals such as radio frequency, microwave, or other electromagnetic frequencies. Alternatively, pressure (patient-applied or otherwise) mechanical, magnetic, or other methods of communication may be utilized to signal allowing for drainage only at selected times. The valve of the device can take many shapes and the device can be manufactured from any of a variety of materials provided that they are biocompatible.

The fluid management system may also be configured to incorporate a pump 16, as shown in FIG. 7. Pump 16, when placed subcutaneously, can be actuated to provide an active pumping mechanism with or without the use of passive or active valves, as described in further detail below. Pump 16 may be configured as a unidirectional pump to facilitate fluid transfer in a single direction. This unidirectional pump feature may be utilized in place of the valve or in combination with the valves.

The patient may optionally perform maneuvers to help increase the pressure of any fluid which may be contained within the body cavity. For instance, the patient may bear down to increase intra-abdominal pressure to facilitate drainage of the peritoneal cavity. Alternatively, the patient may also wear or apply a girdle designed to increase abdominal pressure or apply a urethral catheter to decrease bladder pressure.

Figure 8C:
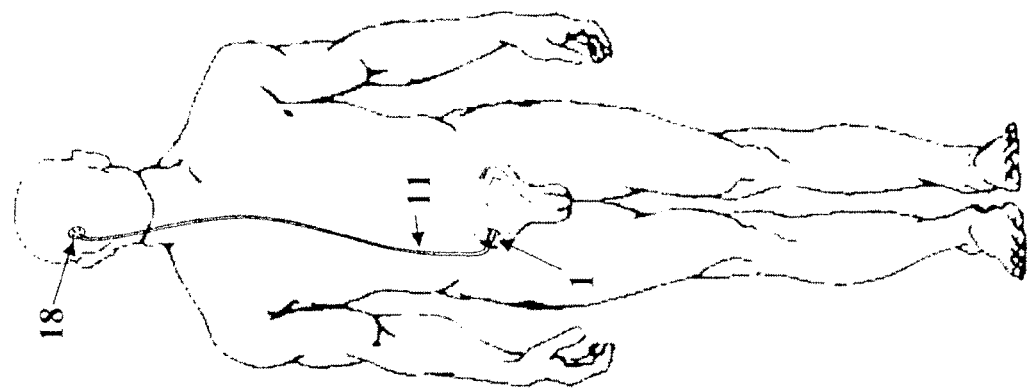
FIGS. 8A to 8C show illustrations of a few of the alternative variations of the drainage system in which the peritoneal cavity, the pulmonary space, and the ventricular space are able to be drained.
Figure 8B:
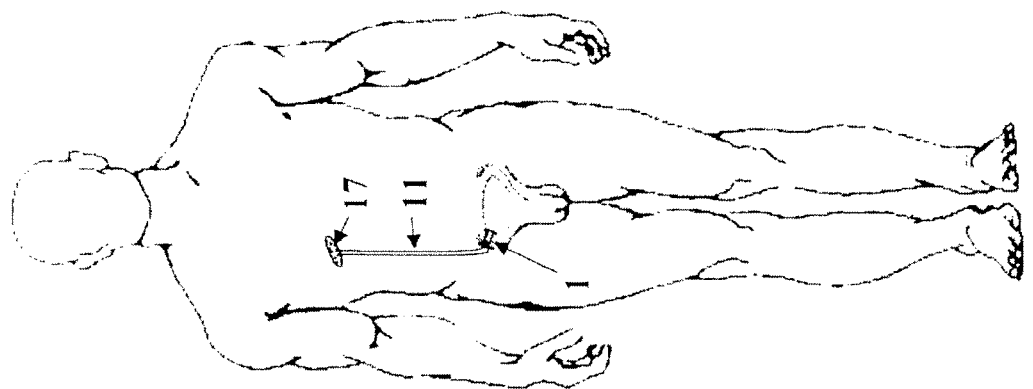
Figure 8A:
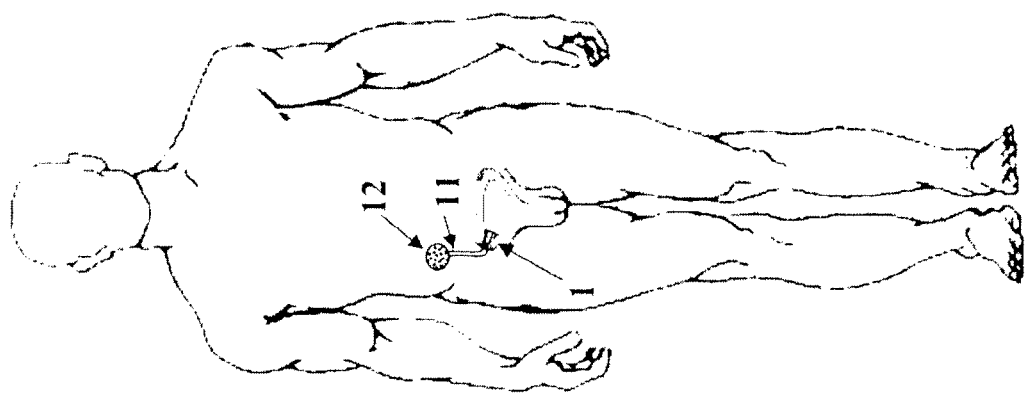

The fluid management system may be configured to drain fluid collections from a variety of different regions within the body. For example, while the shunt 1 may be anchored within the bladder wall, the receptacle 12 may be placed, as described above, within the peritoneal cavity as shown in FIG. 8A. Another example is shown in FIG. 8B where the receptacle 17 may be positioned within the pulmonary space for draining pulmonary effusions and FIG. 8C shows an example where the receptacle 18 may be positioned within the cerebrospinal region for draining excess cerebrospinal fluid. In another variation, a receptacle may be positioned within the pericardial region for draining pericardial effusions.

In yet another variation, the shunt, pump, or tubular devices may incorporate one or several anti-infective agents to inhibit the spread of infection between body cavities. Examples of anti-infective agents which may be utilized may include, e.g., bacteriostatic materials, bacteriocidal materials, one or more antibiotic dispensers, antibiotic eluting materials, entrained radioisotopes, heating elements, bioactive plastics, surfaces which encourage epithelialization, and coatings which prevent bacterial adhesion, and combinations thereof.

Additionally, the devices may also incorporate anti-clogging agents. Examples of anti-clogging agents may include, e.g., active ultrasonic components, an inner and outer sleeve which, when actively agitated through coupling to the pump drive or through a flow driven mechanism, disrupts the inner lumen surfaces which encourage epithelialization, enzyme eluting materials, enzyme eluting materials which specifically target the proteinaceous components of ascites, enzyme eluting materials which specifically target the proteinaceous and encrustation promoting components of urine, chemical eluting surfaces, an intermittent plunger mechanism, coatings which prevent adhesion of proteinaceous compounds, and combinations thereof. The anti-infective and/or anti-clogging agents may be infused through the devices via a reservoir contained, for instance, in the pump or in a separate reservoir. Alternatively, the agents may be integrated within or coated upon the surfaces of the various components of the system.

Figure 9:
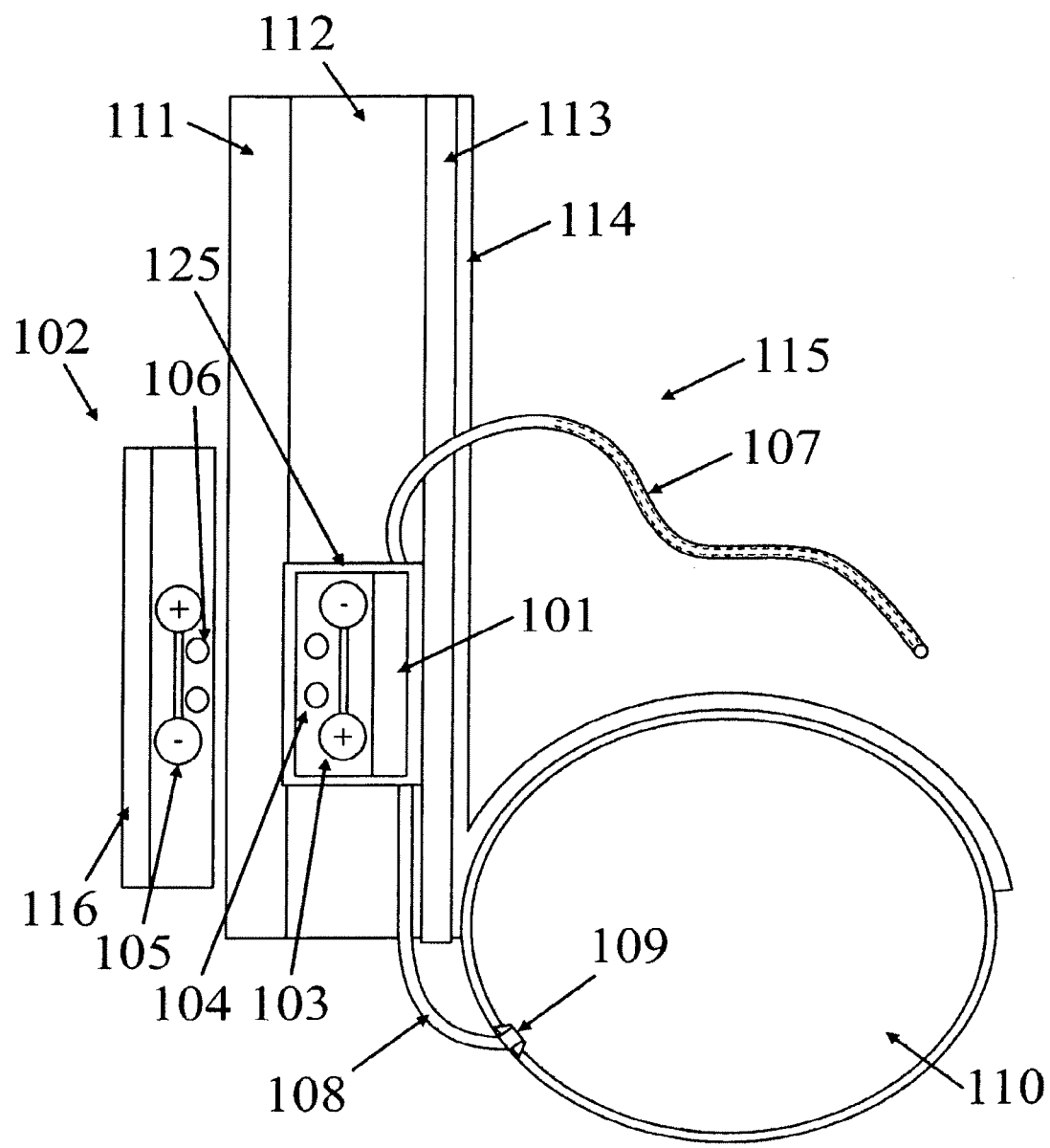
FIG. 9 shows an illustrative magnetically-coupled variation of the drainage system with an illustration of an externally located drive.

FIG. 9 shows an illustrative detail view of another variation of the system of FIG. 7 above. As shown, fluid may be drawn up and carried away by the uptake tube 107, which in this case, has been perforated to prevent blockage. Alternate variations may include an uptake screen at the terminus of the uptake tubing member 107. Although multiple perforations or openings are shown in tubing member 107, a single opening may also be defined at the terminal end of the tubing 107 or along the length of the tubing 107. As mentioned above, the uptake tubing 107 may also include, but is not limited to, conduits, catheters, saphenous arteries or vessels, artificial tubular grafts, etc. The tubing 107 may be positioned where the excess fluid typically collects within the cavity. Tubing 107 may simply be left within the cavity or it may be anchored to a tissue wall via any number of methods for fastening the tubing 107, e.g., sutures, staples, clamps, adhesives, etc.

The uptake tubing 107 leads to the pump 101, which may be used to actively pump or urge the fluid from the uptake tubing 107 and through the outflow tube 108 and into the bladder 110. In this variation, an optional bladder anchor or shunt 109 may be utilized to secure the distal end or portion of outflow tube 108 and prevent detachment of tubing 108 during bladder contraction. The bladder anchor or shunt 109 may be configured in any one of the variations as described above for the shunt 1.

The pump 101, can be powered and operated by electromechanical forces or magnetic coupling. The pump 101 may be placed under the skin 111 in either the subcutaneous space 112 or in the musculature of the abdominal wall 113. The pump 101 may be configured as a peristaltic pump, but may also be a gear-pump, turbine-pump, impeller-pump, radial-flow-pump, centrifugal-pump, piston-pump, or any other suitable pump type. Ideally, the pump 101 design ensures uni-directional operation. Moreover, the pump 101 may be configured to incorporate a pulsatile or oscillating mechanism within the pump 101 to aid in jarring free any materials from collecting or becoming encrusted to thereby prevent the pump 101 or tubing from clogging. However, valves may be configured to ensure unidirectional operation. The pump 101 is preferably enclosed in a housing, shroud or casing 125 made of any suitable biocompatible material.

Also enclosed in the pump housing 125, in this particular variation, is the magnetically-coupled drive. One, two, or more magnets 103 may be provided to operate the pump 101. A separate control module 116 which is remotely located from the implanted pump 101 may be used to drive external magnets 105 located within the drive unit 102 or magnets 105 may be used to provide an oscillating or alternating electromagnetic field to correspondingly couple through the skin 111 with a magnetic field of the implanted magnets 103 located within the pump 101. By rotating or oscillating the magnets 105 in the drive unit 102, the implanted magnets 103 are stimulated or urged to move, thereby transferring their kinetic force to operate the pump 101. While FIG. 9 shows a drive unit 102 with a motor and a linkage, any magnetic field capable of causing or urging the pump magnets 103 to rotate could be used to operate the pump. Furthermore, in order to reduce the torque seen by tissues adjacent to the implanted pump, the pump may utilize a gear mechanism whereby the external drive rotates or oscillates two elements in opposite direction thereby canceling any torques generated. Alternatively, the pump 101 could be electromechanically powered through an implanted battery with external activating and/or monitoring without the requirement for magnetic coupling in which case drive unit 102 may be configured to function as a remote switch for activating the pump 101. One or more sensors may be integrated into the implanted pump 103 for detecting a variety of fluid and/or pump parameters. For instance, FIG. 9 shows at least one sensor 104 integrated within implanted pump 101. A corresponding sensor 106 may be built into the interface of the external drive 102. Both sensors 104 and 106 may be positioned within their respective units such that when the drive 102 is optimally aligned with implanted pump 101, the sensors 104, 106 may indicate to the physician or patient that the pump 101 and drive 102 are optimally engaged and able to efficiently transfer power and/or information. The drive 102 or some other indicator may be used to convey the presence of an optimal engagement to the physician or patient through a variety of methods, for instance, a visual message or indicator signal such as a light or audible signal may be initiated once the sensors 104, 106 have been aligned. These sensors 104, 106 may also transfer information from the pump 101 to the drive 102, and/or from the drive 102 to the pump 101, during operation to monitor fluid pressures and/or fluid flows. Alternatively, additional magnets could also be utilized to anchor the pump 101 to the drive 102 against rotational forces generated during the power transfer operation.

Figure 10A:
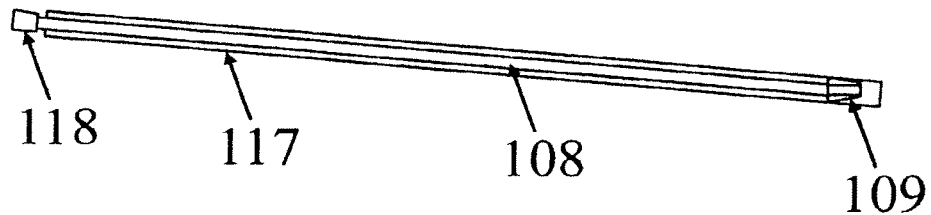
FIGS. 10A to 10C show a variation of the drainage system in which the tubes and pump may be removably attachable allowing for increased ease of insertion.
Figure 10B:
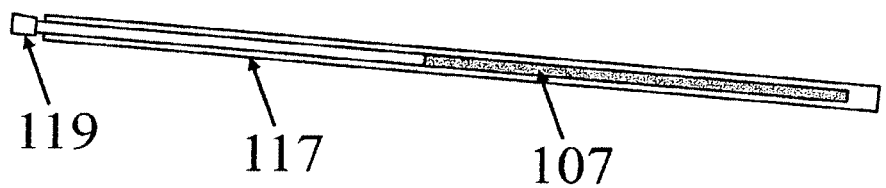
Figure 10C:
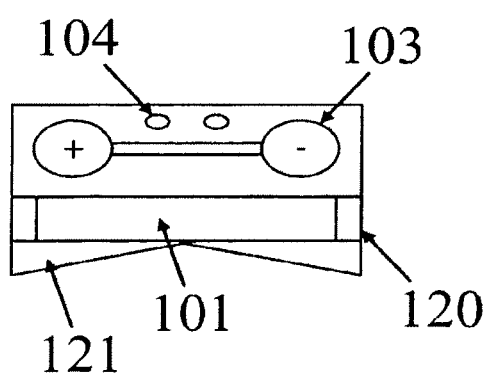

The individual implantable components of the system are shown in detail in FIGS. 10A to 10C. In FIG. 10A, the outflow tubing 108 is shown in one variation in its insertion trocar 117. Also illustrated are the bladder anchor 109 and an optional removably attachable port 118 which may be designed to couple with an insertion port 120 on the pump 101. FIG. 10B illustrates one variation of the inflow drainage tubing 107 in an insertion trocar 117 with an optional removably attachable port 119. Although these variations show the tubing 107, 108 positioned within insertion trocars 117 for deployment within a patient, the tubing 107, 108 may be implanted through various other methods as may be contemplated by one of ordinary skill in the art.

FIG. 10C illustrates one variation of the implantable pump 101 with tubing detached. The pump 101 is illustrated with anchors 121 to resist rotational forces generated with pump use. The pump housing 125 may be anchored by barbed insertion pins 121 and/or materials designed to promote fibrotic ingrowth for anchoring the pump 101 within the muscle 113 or subcutaneous space 112. Alternative variations of the pump device 101 may use other anchoring mechanisms, e.g., screw threading defined on outside surfaces of pump 101, staples, sutures, adhesive compounds, a porous solid promoting interstitial cell growth, one or more pins designed to be inserted into the abdominal wall, etc., and combinations thereof. In the variation shown, the tubing 107, 108 and pump 101 are separate components and may placed individually. For instance, the two tubes 107, 108 may be first inserted through a single incision in the skin and placed in their approximate positions within the patient. The pump 101 may then be inserted through the incision and attached to both tubes 107, 108 and secured at the implantation site. Alternatively, the tubing 107, 108 may be attached to the pump 101 prior to implantation or during manufacture and the entire system may be implanted as a single system.

Figure 11A:
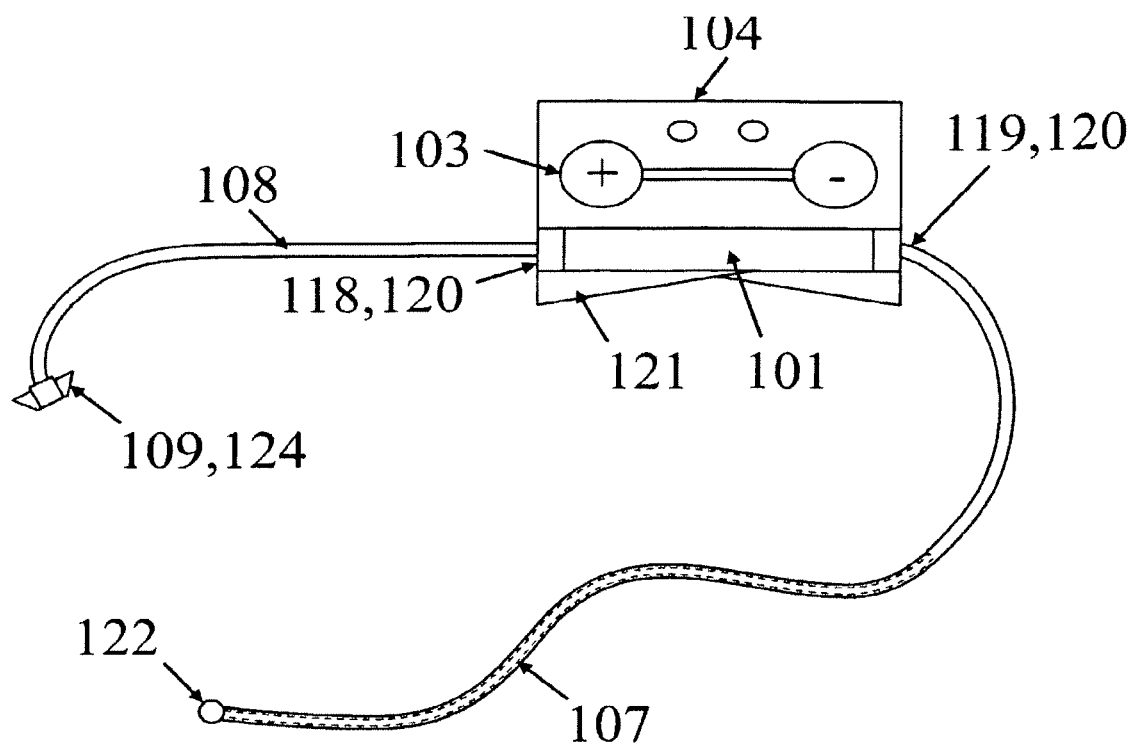
FIG. 11A shows an implantable pump variation having removably attachable tubing in the attached position.

FIG. 11A illustrates the pump 101 and tubing 107, 108 of FIGS. 10A to 10C in which the tubing 107, 108 has been attached to the corresponding outflow and inflow ports of pump 101 at the junctures of tubing port 118 to pump 120 and tubing port 119 to pump 120. Also shown are optional sensors 122, 124 on the ends of the inflow tubing 107 and outflow tubing 108, respectively. One or both of these sensors 122, 124 may be configured to sense any one of a number of fluid parameters. For instance, one or both sensors 122, 124 may detect fluid pressures and/or various chemical parameters such as pH of the fluid, or the presence of certain chemicals, etc. One or both sensors 122, 124 may also be configured to provide positive and/or negative feedback to the control mechanism, such as the externally located drive unit 102 or an integrated controller located within the pump 101, in the control of fluid flows. Although both sensors 122, 124 are shown located at the terminal ends of tubing 107, 108, respectively, they may optionally be located anywhere along the lengths of their respective tubes 107, 108, if desired or necessary.

Figure 11B:
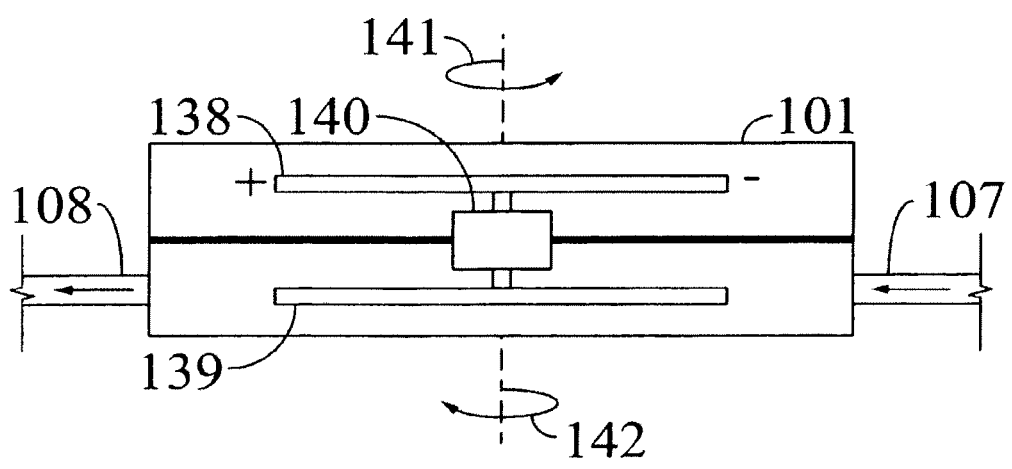
FIG. 11B shows a variation on an implantable pump which may have its moment forces generated by the pump balanced.

FIG. 11B shows a cross-sectional view of another variation of pump 101 which may be utilized to effectively eliminate any excessive movement which may be imparted by torquing forces generated by the pump 101. After pump 101 has been implanted within a patient, it is generally desirable to inhibit movement of the pump 101 within the body. This may be accomplished through a variety of methods, such as securely anchoring the pump 101 to the surrounding tissue. This pump variation may also be configured to reduce any torque which may be seen by tissues adjacent to the implanted pump 101. This may be accomplished, in part, by utilizing at least two counter-rotating or counter-oscillating elements within the pump 101 which may rotate or oscillate during pumping such that oppositely generated moments or rotational moments effectively cancel out or balance each other. As seen in this variation, if a driver unit, such as that described above, were activated to rotate element 138 in a first direction, a first rotational moment 141 is generated. This moment 141, if unbalanced, may impart forces from the pump 101 to the surrounding tissue potentially resulting in damage to the tissue. Element 138 may be rotationally coupled to a gear box 140 which may be configured to reverse the imparted direction of rotation such that element 139, which is also rotationally coupled to gear box 140, is compelled to rotate in an opposite direction from element 138 thus creating a rotational moment 142. The opposite rotational moments 141, 142 may effectively balance or cancel one another such that the net force imparted by the pump 101 to the surrounding tissue is minimized, potentially to a zero load. The counter-rotating or counter-oscillating (depending upon the type of pump utilized) elements within a pump may be balanced in mass and in configuration in any number of ways to optimize the resulting effect on the pump, depending upon the desired effects.

Figure 12A:
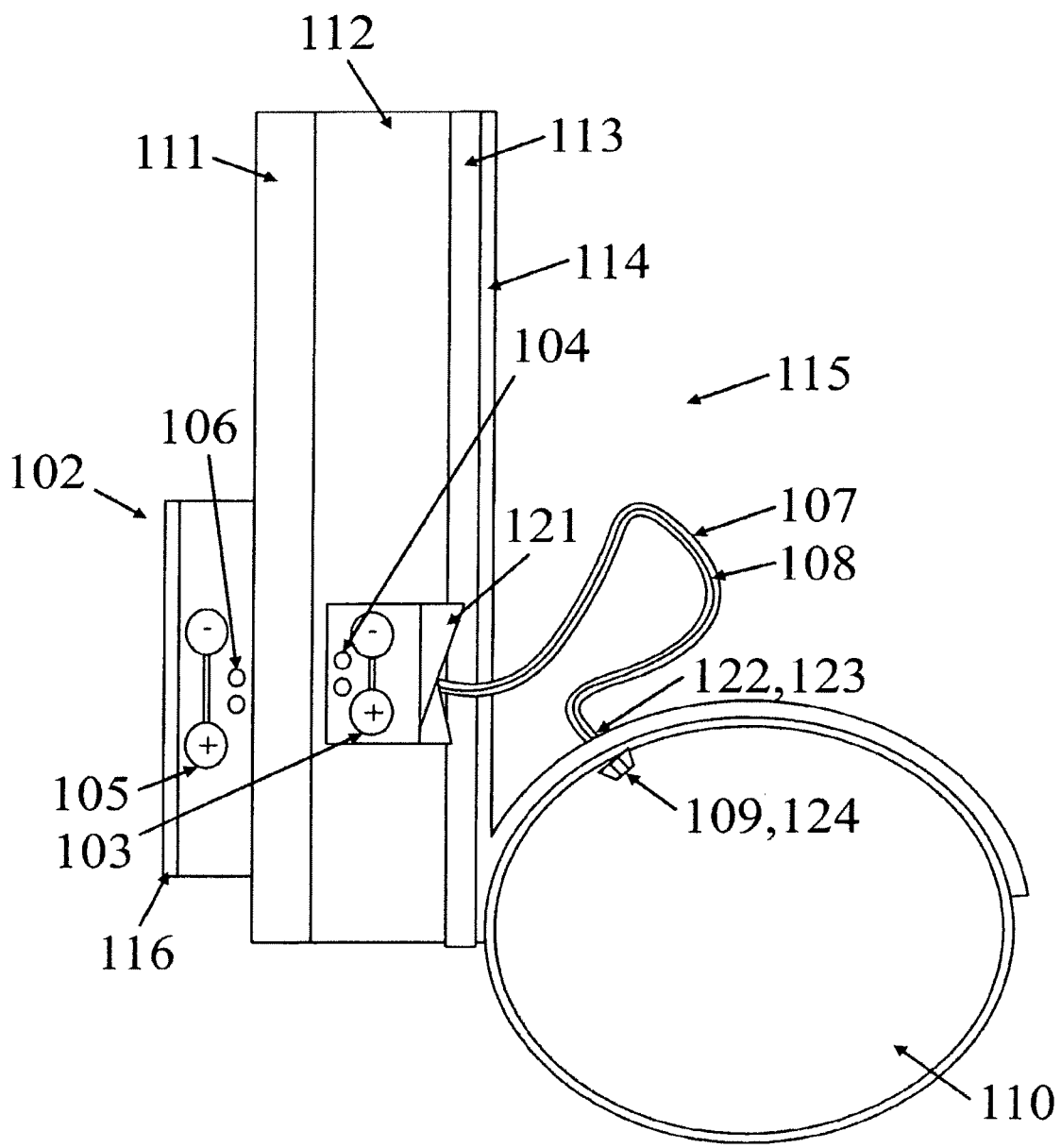
FIG. 12A shows a variation of the drainage system having a single dual-lumen tube.

FIG. 12A illustrates one variation of the fluid management system in which both inflow 107 and outflow 108 tubing share a common wall. This arrangement may be utilized ideally for the peritoneal fluid draining design because the bladder 110 and peritoneal cavity 115 share a common wall which facilitates the insertion of a single dual-lumen tube. Also shown is flange 123 which can be utilized to prevent insertion of the inflow tubing 107 into the bladder 110 in the case of the single-puncture placement. Moreover, any one of the shunt 1 variations described above may be utilized with this variation.

Figure 12B:
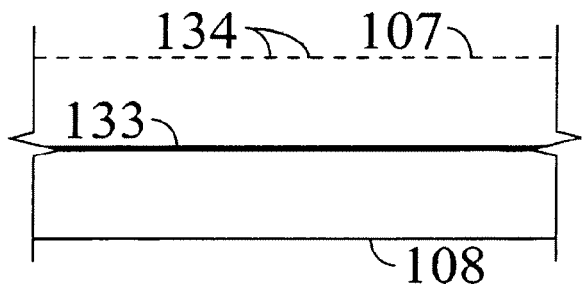
FIGS. 12B to 12G show additional variations of the single dual-lumen tube.
Figure 12C:
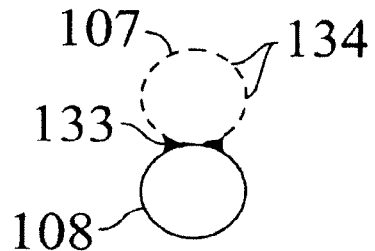
Figure 12D:
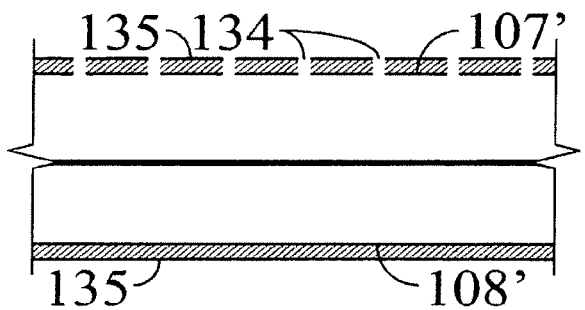
Figure 12E:
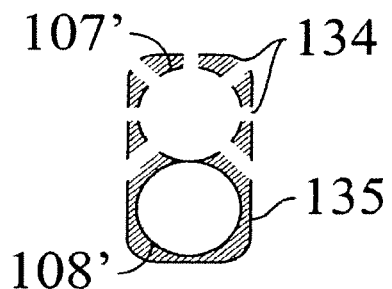
Figure 12F:
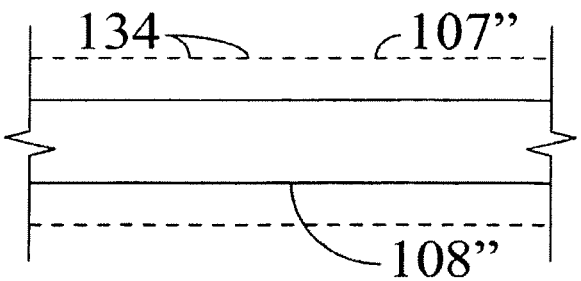
Figure 12G:
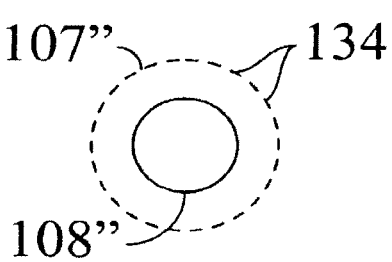

FIGS. 12B and 12C show cross-sectional side and end views, respectively, of the tubing variation of FIG. 12A. As shown, inflow tubing 107 and outflow tubing 108 may share common wall 133, which may be reinforced to maintain the structural integrity of the tubing. The inflow tubing 107 may define one or a plurality of openings 134 for drawing the fluid within tubing 107. Openings 134 may be defined along just a portion of tubing 107 or it may be defined along a majority of the length of tubing 107 depending upon the desired application. In operation, the fluid within the body cavity may be drawn into tubing 107 through openings 134 and drawn into pump 103. The fluid may then be passed through outflow tubing 108 in the opposite direction as the fluid flowing through inflow tubing 107 and subsequently into the bladder 110. FIGS. 12D and 12E show another variation of tubing 107' and 108' in which both tubes are formed from a single extrusion 135. In this variation, tubing 107' may define one or a plurality of openings 134. FIGS. 12F and 12G show cross-sectional side and end views of yet another variation of a single-tube dual-lumen variation in which outflow tubing 108" may be coaxially positioned within inflow tubing 107". In this variation, openings 134 may be defined along a length of inflow tubing 107" while outflow tubing 108" may remain intact.

Both inflow and outflow tubing, or just one of the tubes, may be reinforced along a portion of its length of along its entire length. Reinforcement of the tubing may be accomplished via ribbon or wire braiding or lengths of wire or ribbon embedded or integrated within or along the tubing. The braiding or wire may be fabricated from metals such as stainless steels, superelastic metals such as nitinol, or from a variety of suitable polymers.

Figure 13:
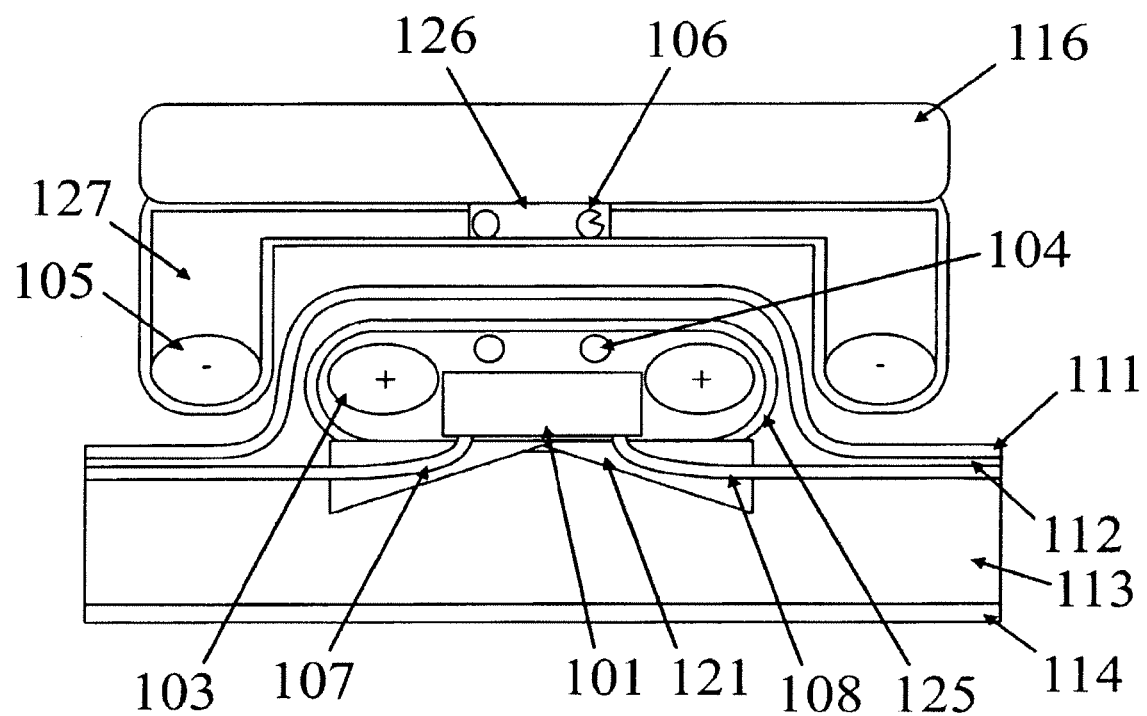
FIG. 13 shows a magnetically-coupled variation of the pump and external drive in which the magnetic interaction is circumferential.

FIG. 13 illustrates one variation of the pump device in which the magnetic coupling mechanism employed allows for circumferential interaction. As shown, the pump 101 may be implanted under the skin 111 yet close to the surface such that the pump magnets 103 may be positioned within the inner diameter of, and/or in the same plane as, the external drive magnets 105. The arms 127 of the drive unit may protrude to define a circumferential cavity for receiving the implanted pump 101 and the overlying skin 111 within this channel. The design of the holding arms 127 may be blunted to prevent excessive pressure from being exerted upon the skin 111 over the site of insertion. In this variation, the driveshaft 126 is shown which transfers power to the magnet holding arm 127 of the drive. This design can also employ one or several pump anchors 121, sensors 104, 106 and/or other features and combinations of the pump and tubing.

Figure 14:
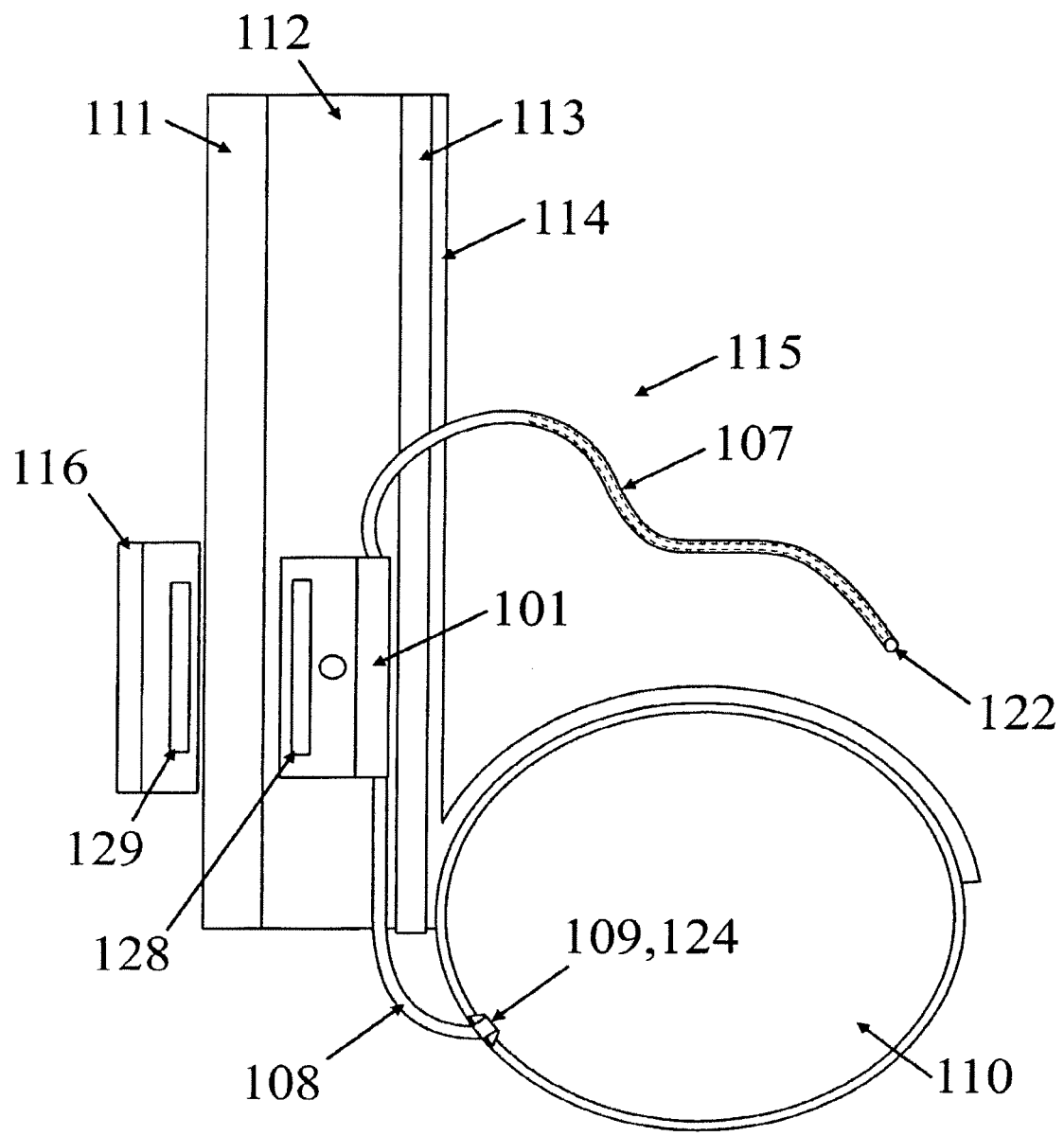
FIG. 14 shows an illustration of an electromechanical variation of the system in which the implanted pump may be rechargeable.
Figure 15:
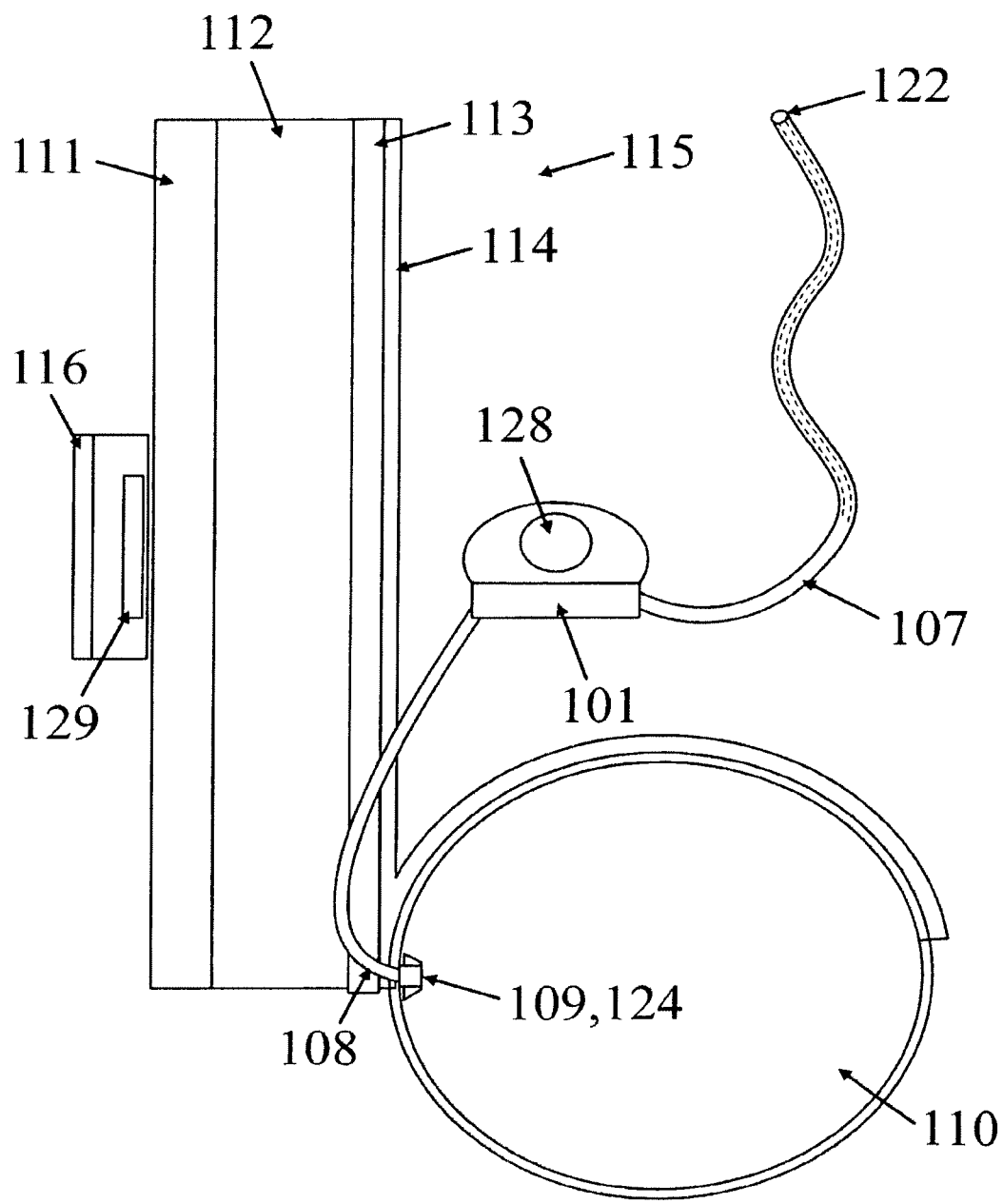
FIG. 15 shows an illustration of an electromechanical variation of the device in which the implanted pump may be placed in a non-subcutaneous position.

FIGS. 14 and 15 illustrate non-magnetically powered pumps in which the implanted pump may be powered by a battery or other implantable power source. In this instance the pump 101 may communicate with the external interface 116 using radiowave or electromagnetic signal generators and receivers 128, 129 to transfer information and/or activation signals. This pump 101 can be placed subcutaneously (as shown in FIG. 14) or in any other region suitable for implantation (for instance, the pump 101 of FIG. 15 may be implanted directly within the peritoneal cavity) so long as it can communicate with the external component 116. The pump can also be internally controlled using the sensors 122, 124 to determine when to activate the pump. These variations may be configured so that the physician or patient may be able to intervene using the external control mechanism 116 in order to prevent the operation of the pump 101 in undesirable circumstances. For example, if the sensors detect negative feedback, the physician and/or patient may activate the pump 101 using the external controls 116 at their discretion. The controls, though, may be easily programmed to incorporate various parameters such as a maximum drainage per day and simple drainage controls such as no drainage when the bladder exceeds a certain pressure. The pump 101 can also be programmed to be activated under certain circumstances, e.g., once the peritoneal pressure sensor 122 experiences a pressure above a certain threshold.

Figure 16:
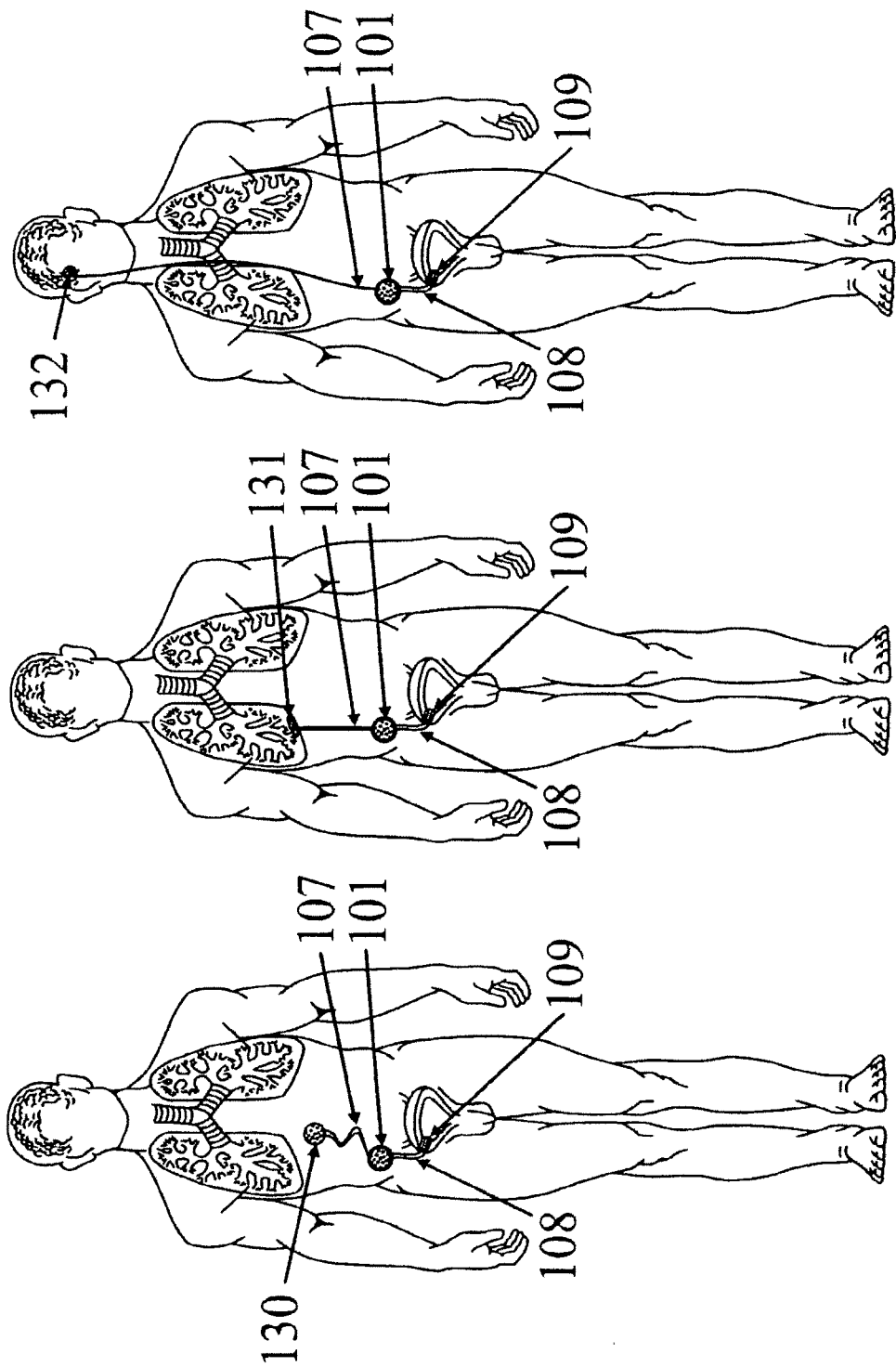
FIGS. 16A to 16C show illustration of a few of the possible uses of the drainage system in the drainage of chronic fluid collections in various regions of the body.

The device may be designed to drain a variety of different fluid collections including, but not limited to, the excess fluid within the peritoneal cavity, as shown in FIG. 16A, pulmonary effusions, as shown in FIG. 16B, and excessive cerebrospinal fluid, as shown in FIG. 16C. These figures show the bladder anchor 109, the outflow tube 108, the pump 101, the inflow tube 107, and the drainage ports for the peritoneal 130, pleural 131 and cerebrospinal 132 drainage sites, although other variations utilizing different features, such as the single tube, dual-lumen tubing described above may be substituted in further variations. Moreover, drainage from other regions of the body using the system and variations thereof are contemplated, such as application for drainage of pericardial effusions. It is important to note that any feature of the present invention can be incorporated into any these designs.

The housing, shroud or casing 125 of the pump can take many shapes and the pump housing 125 can be manufactured from any of a variety of biocompatible materials. Alternatively, the pump housing 125 may incorporate anti-infective components or agents in order to prevent the spread of infection between the body cavities. Such anti-infective components or agents may include, e.g., bacteriostatic materials, bacteriocidal materials, one or more antibiotic dispensers, antibiotic eluting materials, entrained radioisotopes, heating elements, bioactive plastics, surfaces which encourage epithelialization, coatings which prevent bacterial adhesion, etc., and combinations thereof. Alternatively, the device may also incorporate anti-clogging components, e.g., active ultrasonic components, surfaces which encourage epithelialization, enzyme eluting materials, chemical eluting surfaces, coatings which prevent adhesion of proteinaceous compounds, etc., and combinations thereof.

The device has been designed to allow for minimally invasive placement, ideally through the use of non-invasive radiographic imaging tools such as abdominal ultrasound. Placement of the fluid management system may be facilitated by filling the bladder 110 and using ultrasound to locate this space; the outflow tubing 108 can then be placed through a small incision and a simple puncture. The inflow tubing 107 can also be placed in a similar manner using subcutaneous tunneling of the tubing and ultrasound guidance. Once the tubing has been placed, the outflow tubing 107 and the inflow tubing 108 may then be attached to the pump 101 at the insertion sites. The pump 101 may then be set into its site of implantation (for instance, in the subcutaneous space) after which the wound is closed and allowed to heal.

Figure 17:
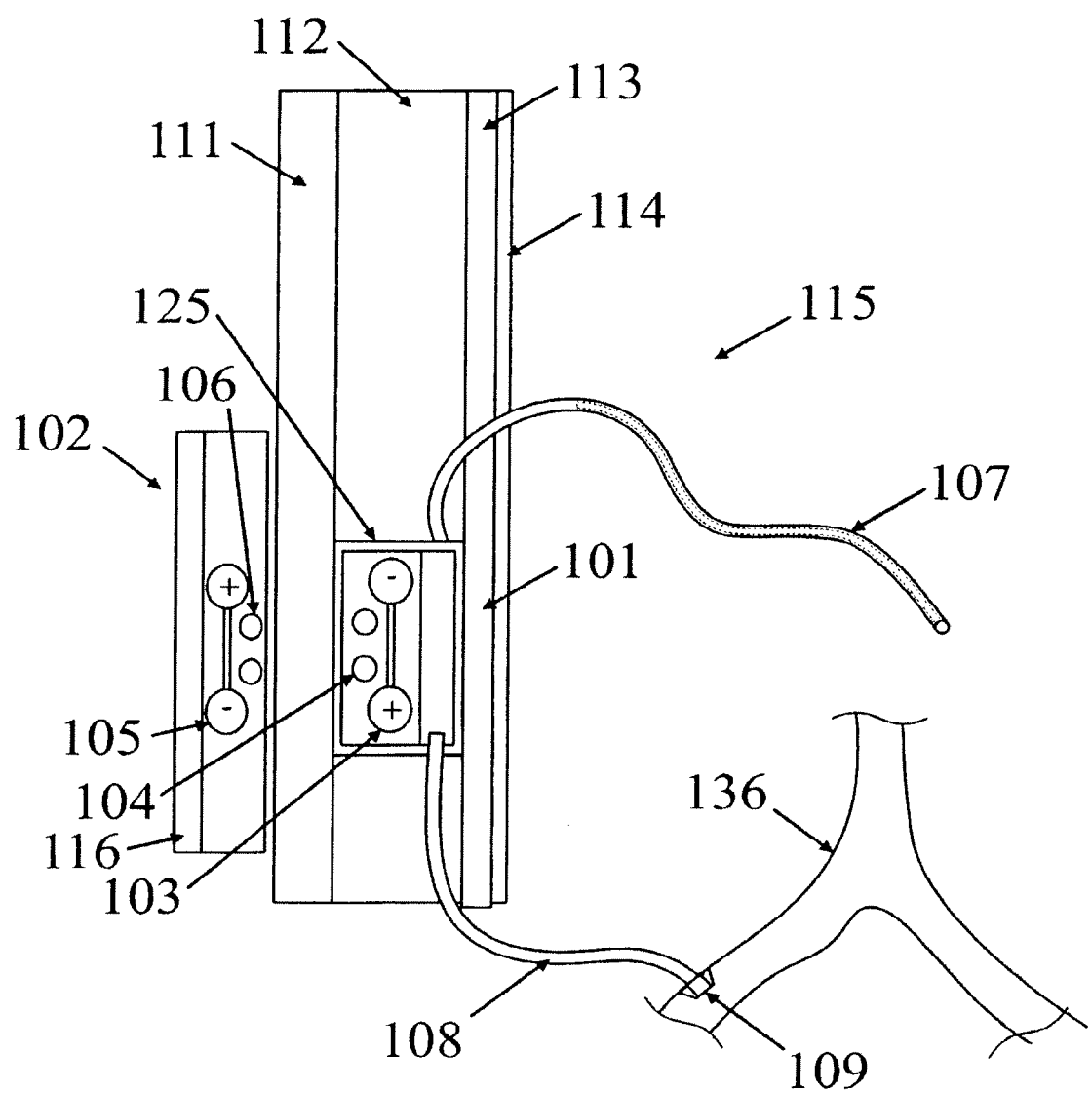
FIG. 17 shows a variation of the drainage system which may be fluidly coupled to the vascular system.

Another application for the fluid management system may be seen in FIG. 17, which shows outflow tubing 108 fluidly coupled in a fluid-tight seal to the vasculature 136 of the patient. The fluid collected through inflow tubing 107 may be urged via pump 101 through outflow tubing 108 and passed into the vasculature 136 via an anastomotic connection at one of any number of suitable locations along the vasculature. In such a variation, the outflow tubing 108 may be a saphenous vein or artery. The anastomotic connection between tubing 108 and the vasculature is preferably a fluid-tight seal and may be accomplished through any variety of methods as known to one of skill in the art.

Figure 18:
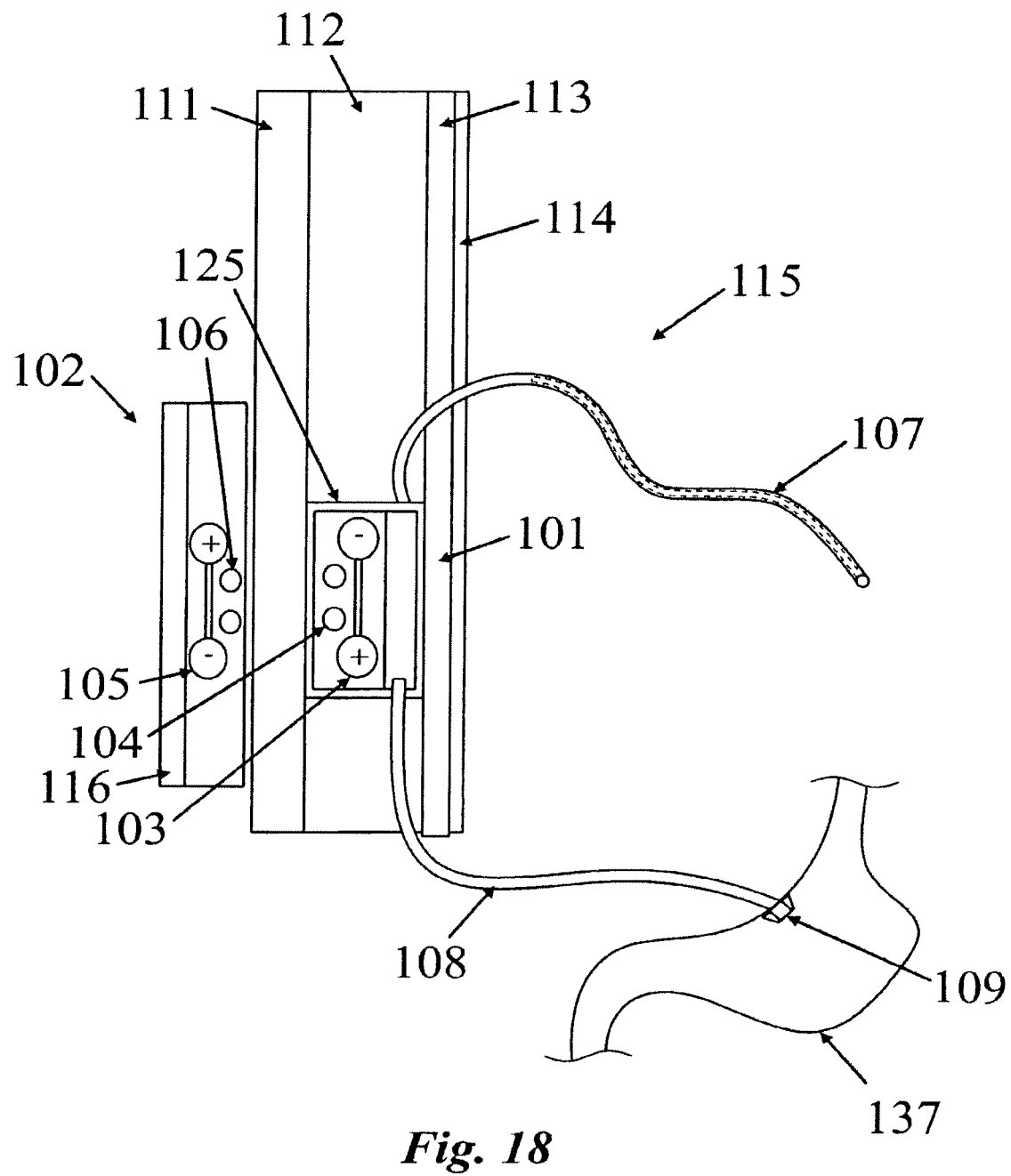
FIG. 18 shows another variation of the drainage system which may be coupled to a stomach or another portion of the gastro-intestinal system.

Yet another variation is shown in FIG. 18, which shows outflow tubing 108 fluidly connected to a stomach 137 of the patient. The collected fluid may be passed into the stomach 137 through use of the shunt described above or through another anastomotic connection to allow for the absorption of any additional nutrients which may be present in the excess fluid. The fluid urged into the stomach may then be passed through the gastro-intestinal system of the patient and eventually voided from the body. Although this example shows fluid connection to the stomach 137, outflow tubing 108 may alternatively be coupled to other suitable regions of the gastro-intestinal tract, such as regions of the small and large intestinal tracts.

While the device is primarily contemplated for use in human patients, the invention will also have veterinary uses or product development purposes in equine, bovine, canine, feline, and other mammalian species.

The applications of the devices and systems discussed above are not limited to certain treatments, but may include any number of other maladies. Modification of the above-described methods for carrying out the invention, and variations of the mechanical aspects of the invention that are obvious to those of skill in the arts are intended to be within the scope of the claims. Moreover, various combinations of aspects between examples is also contemplated and is considered to be within the scope of this disclosure.

The invention claimed is:

1. An implantable fluid management system comprising:
   an implantable pump having an inlet, an outlet, an electromechanical motor and an integrated controller, the implantable pump configured to be implanted subcutaneously;
   a first tube coupled between a pleura and the inlet;
   a first pressure sensor disposed in fluid communication with the first tube and operatively coupled to the controller;
   a second tube coupled between the outlet and a bladder; and
   a second pressure sensor disposed in fluid communication with the second tube and operatively coupled to the controller,
   wherein the integrated controller is programmed to activate the electromechanical motor to pump fluid from the pleura to the bladder responsive to the first pressure sensor detecting a fluid parameter in the pleura exceeding a first predetermined threshold and the second sensor detecting a fluid parameter in the bladder lower than a second predetermined threshold.

2. The system of claim 1, wherein the implantable pump further comprises an external control module configured to be periodically coupled to the implantable pump to transfer energy to the implantable pump.

3. The system of claim 2, wherein the external control module comprises a driveshaft and a magnet holding arm, the driveshaft transferring power to the magnet holding arm.

4. The system of claim 2, wherein the external control module transfers the energy to the implantable pump.

5. The system of claim 1, wherein the implantable pump further comprises a housing having anchors.

6. The system of claim 5, wherein the anchors are selected from the group consisting of barbed insertion pins, a screw threading defined on an outside surface of the implantable pump, staples, sutures, adhesive compounds, a porous solid promoting interstitial cell growth, one or more pins designed to be inserted into the abdominal wall, and combinations thereof.

7. The system of claim 5, wherein the housing comprises a material promoting fibrotic ingrowth into the housing.

8. The system of claim 5, wherein one or more anti-infective coatings are provided on the housing.

9. The system of claim 1, wherein the first pressure sensor is disposed at an end of the first tube and the second pressure sensor is disposed at an end of the second tube.

10. The system of claim 1, further comprising a housing made of a biocompatible material.

11. The system of claim 1, wherein the implantable pump and integrated controller are configured to be remotely activated.

12. The system of claim 1, wherein the implantable pump further comprises a battery.

13. A method of removing fluid from a pleura, the method comprising:
   subcutaneously implanting a pump, a first tube, a first pressure sensor, a second tube, and a second pressure sensor such that the first tube is coupled between the pleura and an inlet of the pump, the first pressure sensor is disposed in fluid communication with the first tube, the second tube is coupled between a bladder and an outlet of the pump, and the second pressure sensor is disposed in fluid communication with the second tube;
   activating the pump to pump fluid from the pleura to the bladder responsive to the first pressure sensor detecting a fluid parameter in the pleura exceeding a first predetermined threshold and the second sensor detecting a fluid parameter in the bladder lower than a second predetermined threshold.

14. The method of claim 13, wherein the pump further comprises an external control module configured to be periodically coupled to the pump to transfer energy to the pump.

15. The method of claim 14, wherein the external control module transfers the energy to the pump.

16. The method of claim 13, wherein the pump further comprises a biocompatible housing having anchors.

17. The method of claim 16, wherein the anchors are selected from the group consisting of barbed insertion pins, a screw threading defined on an outside surface of the implantable pump, staples, sutures, adhesive compounds, a porous solid promoting interstitial cell growth, one or more pins designed to be inserted into the abdominal wall, and combinations thereof.

18. The method of claim 16, wherein the housing comprises a material promoting fibrotic ingrowth into the housing.

19. The method of claim 13, wherein activating the pump comprises remotely activating the pump.

20. The method of claim 13, wherein the pump further comprises a battery.

* * * * *